(12) United States Patent
Engelhardt et al.

(10) Patent No.: US 11,633,383 B2
(45) Date of Patent: Apr. 25, 2023

(54) DOSAGE PRINCIPLE FOR DRUGS USEFUL FOR TREATING NEOPLASTIC DISEASES

(71) Applicant: Basilea Pharmaceutica International AG, Basel (CH)

(72) Inventors: Marc Engelhardt, Basel (CH); Anne Schmitt-Hoffmann, Basel (CH); Patrice Larger, Basel (CH)

(73) Assignee: Basilea Pharmaceutica International AG, Basel (CH)

( * ) Notice: Subject to any disclaimer, the term of this patent is extended or adjusted under 35 U.S.C. 154(b) by 110 days.

(21) Appl. No.: 16/611,524

(22) PCT Filed: May 15, 2018

(86) PCT No.: PCT/EP2018/062601
§ 371 (c)(1),
(2) Date: Nov. 7, 2019

(87) PCT Pub. No.: WO2018/210868
PCT Pub. Date: Nov. 22, 2018

(65) Prior Publication Data
US 2020/0237730 A1 Jul. 30, 2020

(30) Foreign Application Priority Data
May 16, 2017 (EP) .................................... 17171226

(51) Int. Cl.
*A61K 31/4245* (2006.01)
*A61K 9/00* (2006.01)

(52) U.S. Cl.
CPC ........ *A61K 31/4245* (2013.01); *A61K 9/0019* (2013.01)

(58) Field of Classification Search
CPC .... A61K 31/4245; A61K 9/0019; A61P 35/00
See application file for complete search history.

(56) References Cited

U.S. PATENT DOCUMENTS 8,802,858 B2 * 8/2014 Pohlmann ............... A61P 43/00
546/269.4

FOREIGN PATENT DOCUMENTS

| WO | 2004103994 A1 | 12/2004 |
|---|---|---|
| WO | 2011012577 A1 | 2/2011 |
| WO | 2012098203 A1 | 7/2012 |
| WO | 2012098207 A1 | 7/2012 |
| WO | 2012098208 A1 | 7/2012 |
| WO | 2012113802 A1 | 8/2012 |
| WO | 2012130887 A1 | 10/2012 |
| WO | 2015173341 A1 | 11/2015 |
| WO | 2017068182 A1 | 4/2017 |
| WO | 2018197475 A1 | 11/2018 |
| WO | 2019097073 A1 | 5/2019 |

OTHER PUBLICATIONS

Gilbert, "Multi-Parametric Analysis of HCS Data," The Hunter Meeting 22.—Mar. 25, 2011, Pokolbin, Australia.
Gupta, "Delineation of Current Development of Antimitotic Compounds Targeting Cytoskeletal Protein Tubulin and Microtubule in the Cancer Therapy," Current Chemical Biology, 2014, 8, 165-183.
Heidi Lane, "Breast Cancer Drug Screening Models," Basel Breast Consortium, Jun. 14, 2016.
Heidi Lane, "Targeted Development of Anticancer Agents," Friedrich Miescher Institute Symposium, Basel, Jun. 26, 2015.
Heidi Lane, "BAL101553 (a prodrug of BAL27862) a Novel Microtubule Targeting Agent for the Treatment of Cancer Patients," 2013-NCCR Chemical Biology Seminar, Geneva, Presentation.
Heidi Lane, "Biomarker discovery for the novel microtubule-targeting drug BAL101553 (prodrug of BAL27862)," BIT'S Biopharmaceutical Summit Frankfurt, Germany, Aug. 7-8, 2013.
Heidi Lane, et al., "Abstract 3795: BubR1 function is required for the antiproliferative activity of the novel microtubuletargeting drug BAL27862 (active moiety of the prodrug BAL101553)," Cancer Research 2012 72:8 SUPPL. 1, Abstract nr 3795.
Heidi Lane et al., "BAL27862: A Novel Tubulin Interacting Agent with Activity in Multidrug Resistant Tumors and Potential as a Vascular Disruption Agent," EORTC—NCI—AACR Symposium 2008.
Heidi Lane, et al., "Abstract 3795: BubR1 function is required for the antiproliferative activity of the novel microtubuletargeting drug BAL27862 (active moiety of the prodrug BAL101553)," Cancer Research 2012 72:8 SUPPL. 1, Abstract nr 3795. (Poster).
Heidi Lane, "Patient Stratification Biomarkers for the Novel Microtubule-targeting Drug BAL101553 (prodrug of BAL27862)," 2012-2rd Annual Oncology Biomarkers Congress, Manchester Presentation.
Heidi Lane, "Microtubule Destabilization—A Novel Approach for Cancer Treatment," Drug Discovery and Development 2009, May 15, 2009, Lausanne.
Joerger et al., A phase 1 study to assess the safety, pharmacokinetics (PK), pharmacodynamics (PD) and antitumor activities of BAL101553, a novel tumor checkpoint controller (TCC), clinical oncology. Conference: 2017 annual meeting of the american society of clinical oncology, ASCO, United states, Aug. 31, 2017.
Joerger et al., "A phase I study to assess the safety, pharmacokinetics (PK), pharmacodynamics (PD) and antitumor activities of BAL101553, a novel tumor checkpoint controller (TCC), administered as 48-hour infusion in adult patients with advanced solid tumors," Abstract No. TPS2602 ASCO Annual Meeting, Jun. 2-6, 2017. Poster.
Jonathan Thwaite, PCT application claiming priority from EP17171226.8, letter to EPO, mailed on May 15, 2018.
Kolb et al., "Brief Report Initial Testing (Stage 1) of BAL101553, a Novel Tubulin Binding Agent, by the Pediatric Preclinical Testing Program," Pediatr Blood Cancer 2015;62:1106-1109.

(Continued)

*Primary Examiner* — Kamal A Saeed

(57) ABSTRACT

The present invention provides a novel dosage principle for compounds of formula I and pharmaceutically acceptable derivatives thereof as defined in the claims, wherein said compound or pharmaceutically acceptable derivative thereof is intravenously administered to said patient over a period of at least about 8 hours, wherein the dose of the compound of formula I or pharmaceutically acceptable derivative thereof is at least the molar equivalent of about 45 mg/m$^2$ of the dihydrochloride salt of the compound of formula I-B as defined in the claims.

52 Claims, 3 Drawing Sheets

(56) References Cited

OTHER PUBLICATIONS

Kristeleit et al., "Phase 1/2a trial of daily oral BAL101553, a novel tumor checkpoint controller (TCC), in advanced solid tumors," Kristeleit, R. S. J. Clin. Oncol 35:15 (Abstract), May 30, 2017.
Kristeleit et al., "Phase 1/2a trial of daily oral BAL101553, a novel tumor checkpoint controller (TCC), in advanced solid tumors," Kristeleit, R. S. J. Clin. Oncol. 35:15 (Poster), Jun. 2-6, 2017.
Kristeleit et al., "A Phase 1 study to assess the safety, pharmacokinetics (PK), pharmacodynamics (PD) and antitumor activities of daily oral BAL101553, a novel tumor checkpoint controller (TCC) in adult patients with advanced solid tumors," Journal of Clinical Oncology, 2016 ASCO Annual Meeting (Jun. 3-7, 2016) vol. 34, No. 15_suppl (May 20 Supplement), 2016: TPS2594.
Knsteleit et al., "A Phase 1 study to assess the safety, pharmacokinetics (PK), pharmacodynamics (PD) and antitumor activities of daily oral BAL101553, a novel tumor checkpoint controller (TCC) in adult patients with advanced solid tumors," Journal of Clinical Oncology, 2016 ASCO Annual Meeting (Jun. 3-7, 2016) vol. 34, No. 15_suppl (May 20 Supplement), 2016: TPS2594. (Poster).
Knsteleit et al., "A randomized Phase 2a study to assess pharmacodynamics, antitumor activity and safety of intravenous BAL101553, a novel microtubule inhibitor, at two dose levels in adult patients with selected advanced solid tumors," Journal of Clinical Oncology 33, No. 15_suppl Published online Jan. 31, 2017.
Kristeleit et al., "A randomized Phase 2a study to assess pharmacodynamics, antitumor activity and safety of intravenous BAL101553, a novel microtubule inhibitor, at two dose levels in adult patients with selected advanced solid tumors," Abstract No. TPS2611, ASCO Annual Meeting May 29 to Jun. 2, 2015. (Poster).
Lopez et al., "Phase 1/2a trial of intravenous BAL101553, a novel tumor checkpoint controller (TCC), in advanced solid tumors," Journal of Clinical Oncology, 2016 ASCO Annual Meeting (Jun. 3-7, 2016) vol. 34, No. 15_suppl (May 20 Supplement), 2016.
Lopez et al., "Phase 1/2a trial of intravenous BAL101553, a novel tumor checkpoint controller (TCC), in advanced solid umors," Journal of Clinical Oncology, 2016 ASCO Annual Meeting (Jun. 3-7, 2016) vol. 34, No. 15_suppl (May 20 Supplement), 2016. Poster.
Mladek et al., "Abstract 4781: The novel tubulin-binding 'tumor checkpoint controller' BAL101553 has anti-cancer activity alone and in combination treatments across a panel of GBM patient-derived xenografts," AACR 107th Annual Meeting 2016; Apr. 16-20, 2016.
Mladek et al., "Abstract 4781: The novel tubulin-binding 'tumor checkpoint controller' BAL101553 has anti-cancer activity alone and in combination treatments across a panel of GBM patient-derived xenografts," AACR 107th Annual Meeting 2016; Apr. 16-20, 2016. Poster.
Molife et al., "A First-in-Human Study of Intravenous BAL101553, a Novel Microtubule Inhibitor, in Patients With Advanced Solid Tumors," Annals of Oncology 26 (Supplement 2): ii3-ii5, 2015.
Molife et al., "A first-in-human dose-escalation study of the safety, pharmacokinetics (PK), and pharmacodynamics (PD) of intravenous BAL101553, a novel microtubule inhibitor, in adult patients with advanced solid tumors," Ann Dncol. Mar. 2015;26 (suppl 2):ii3-ii4. (presentation).
Molife et al., "Phase I/IIa trial of the novel microtubule inhibitor BAL101553 in advanced solid tumors: Phase I completed," J Clin Oncol 32:15, 2014 (suppl 1; abstr 2562).
Molife et al., "Phase I/IIa trial of the novel microtubule inhibitor BAL101553 in advanced solid tumors: Phase I completed," J Clin Oncol 32:15, 2014 (suppl 1; abstr 2562). (Poster).
Pohlmann, "An Optimized Prodrug of the Microtubule Destabilizer BAL27862," 2013-14th Annual Drug Discovery Summit, Geneva Presentation.
Pohlmann, "BAL27862—A Dominant Microtubule Destabilizer Active Against Refractory Cancers," GTCbio CancerDrugs Research and Development Feb. 19-20, 2009 Philadelphia, PA.

Pohlmann et al., "BAL27862: A novel oral tubulin interacting agent that overcomes the Pgp—related multidrug resistance phenotype in vitro and in vivo," AACR Annual Meeting—Apr. 14-18, 2007.
Pohlmann et al., "BAL27862: A novel oral tubulin interacting agent that overcomes the Pgp—related multidrug esistance phenotype in vitro and in vivo," AACR Annual Meeting—Apr. 14-18, 2007. (Poster).
Pohlmann et al.,"Abstract 1347: BAL101553: An optimized prodrug of the microtubule destabilizer BAL27862 with superior antitumor activity," Cancer Research 2011 71:8 SUPPL. 1.
Pohlmann et al.,"Abstract 1347: BAL101553: An optimized prodrug of the microtubule destabilizer BAL27862 with superior antitumor activity," Cancer Research 2011 71:8 SUPPL. 1. (Poster).
Pohlmann et al. "Abstract 4419: BAL101553: A highly soluble prodrug of the potent microtubule destabilizer BAL27862," AACR 101st Annual Meeting 2010—Apr. 17-21, 2010.
Pohlmann et al. "Abstract 4419: BAL101553: A highly soluble prodrug of the potent microtubule destabilizer BAL27862," AACR 101st Annual Meeting 2010—Apr. 17-21, 2010. (Poster).
Prota et al., "The Novel Microtubule-Destabilizing Drug BAL27862 Binds to the Colchicine Site of Tubulin with Distinct Effects on Microtubule Organization," J Mol Biol. Apr. 1, 20147;426(8):1848-60.
Rovini et al., "Antitumor Activity of BAL27862 (active Moiety of the Prodrug BAL101553) is Associated with the Generation of Short Non-centrosomal Microtubules," European Journal of Cancer 2012 48 SUPPL. 6(128-).
Rovini et al., "Antitumor Activity of BAL27862 (active Moiety of the Prodrug BAL101553) is Associated with the Generation of Short Non-centrosomal Microtubules," European Journal of Cancer 2012 48 SUPPL. 6(128-). (Poster).
Sharma et al., "LB-151 / 23—The novel tubulin-binding, tumor checkpoint controller BAL101553 has differential effects on tumor vascularization with IV and oral dosing and provides superior anti-tumor activity in combination with bevacizumab," AACR Annual Meeting 2017 Online Proceedings and Itinerary Planner Home, Apr. 3, 2017.
Sharma et al., "The novel tubulin-binding tumor checkpoint controller' BAL101553 has differential effects on tumor vascularization with i.v. and oral dosing and provides superior anti-tumor activity in combination with bevacizumab," AACR Annual Meeting 2017, Poster, Apr. 3, 2017.
Sharma et al., "The novel microtubule-destabilizing drug BAL101553 acts as radiosensitizing agent in treatment refractory tumor models," Strahlenther Onkol, 193:865-876, Aug. 22, 2017.
Sharma et al., "The novel microtubule targeting agent BAL101553 in combination with radiotherapy in treatment-refractory tumor models," Radiother Oncol. Sep. 2017;124(3):433-438.
Sovran, "American Association for Cancer Research 98th Annual Meeting Anticancer agents—Part III," IDrugs 200710 (6):362-365.
Stepanov et al., "A facile synthesis and microtubule-destabilizing properties of 4-(1 Hbenzo[d]imidazol-2-yl)-furazan-3-amines," European Journal of Medicinal Chemistry 94:237-251.
Schmitt-Hoffmann et al., "Abstract C233: BAL27862: A unique microtubule-targeted agent with a potential for the treatment of human brain tumors," AACR-NCI-EORTC International Conference: Molecular Targets and Cancer Therapeutics—Nov. 15-19, 2009.
Schmitt-Hoffmann et al., "Abstract C233: BAL27862: A unique microtubule-targeted agent with a potential for the treatment of human brain tumors," AACR-NCI-EORTC International Conference: Molecular Targets and Cancer Therapeutics-Nov. 15-19, 2009. (Poster).
Burger et al., "BAL101553 (prodrug of BAL27862): The 'Spindle Assembly Checkpoint' is required for anti-cancer activity," 2015-AACR, Abstract 3789, Jun. 20-23, 2015.
The International Search Report and Written Opinion, dated Sep. 11, 2018, in the corresponding PCT Appl. No. PCT/EP2018/062601.
The extended European search report, dated Nov. 3, 2017, in the related European Patent Appl. No. 17171226.8.
Bachmann, "BAL101553 (prodrug of BAL27862): The 'Spindle Assembly Checkpoint (SAC)' is required for anti-cancer activity," 11th Annual Biomarkers Congress Feb. 26-27, 2016, Manchester, UK.

(56) References Cited

OTHER PUBLICATIONS

Bachmann et al., "Abstract 3789: BAL101553 (prodrug of BAL27862): the spindle assembly checkpoint is required for anticancer activity," AACR 106th Annual Meeting 2015; Apr. 18-22, 2015.
Bachmann et al., "Abstract 831: BAL101553 (prodrug of BAL27862): A unique microtubule destabilizer active against drug refractory breast cancers alone and in combination with trastuzumab," AACR Annual Meeting 2014; Apr. 5-9, 2014.
Bachmann et al., "Abstract 831: BAL101553 (prodrug of BAL27862): A unique microtubule destabilizer active against drug refractory breast cancers alone and in combination with trastuzumab," AACR Annual Meeting 2014; Apr. 5-9, 2014. (Poster).
Bachmann et al., "Dual Mechanism of Action of the Novel Microtubuletargeting Drug BAL27862 (active Moiety of the Prodrug BAL101553): Targeting Tumor and Vascular Cells," European Journal of Cancer 2012 48 SUPPL. 6(128-).
Bachmann et al., "Dual Mechanism of Action of the Novel Microtubuletargeting Drug BAL27862 (active Moiety of the Prodrug BAL101553): Targeting Tumor and Vascular Cells," European Journal of Cancer 2012 48 SUPPL. 6(128-). (Poster).
Bachmann et al., "Abstract 743: Development of tumor models resistant to the novel microtubule destabilizer BAL27862 (active moiety of the prodrug BAL101553)," AACR 102nd Annual Meeting 2011—Apr. 2-6, 2011.
Bachmann et al., "Abstract 743: Development of tumor models resistant to the novel microtubule destabilizer BAL27862 (active moiety of the prodrug BAL101553)," AACR 102nd Annual Meeting 2011—Apr. 2-6, 2011. (Poster).
Bachmann et al., "BAL27862: A Novel Tubulin-Interacting Anticancer Agent with Activity in Multidrug Resistant Tumors and Potential as a Vascular Disruption Agent," 2009-Villars Meeting Poster Abstract.
Bachmann et al., "Abstract C229: BAL27862: A novel anticancer agent which dissociates microtubules and creates a distinct cellular phenotype," AACR-NCI-EORTC International Conference: Molecular Targets and Cancer Therapeutics—Nov. 15-19, 2009.
Bachmann et al., "Abstract C229: BAL27862: A novel anticancer agent which dissociates microtubules and creates a distinct cellular phenotype," AACR-NCI-EORTC International Conference: Molecular Targets and Cancer Therapeutics—Nov. 15-19, 2009. (Poster).
Basilea press release, Apr. 6, 2017.
Basilea press release, Jun. 9, 2016.
Basilea press release, Dec. 2, 2016.
Basilea press release, Dec. 28, 2015.
Basilea press release, Nov. 5, 2015.
Basilea press release, Jun. 25, 2015.
Basilea press release, Nov. 19, 2014.
Basilea press release, Jun. 26, 2014.
Garces et al., "A phase I study to assess the safety, pharmacokinetics (PK), pharmacodynamics (PD) and antitumor activities of daily oral BAL101553, a novel tumor checkpoint controller (TCC) in adult patients with progressive or recurrent glioblastoma (GBM) or high-grade glioma," J. Clin. Oncol. 2017 35:15, (Poster), Jun. 2-6, 2017.
Basilea press release, Jun. 6, 2017.
Basilea press release, Apr. 21, 2016.
Basilea press release, Jun. 2, 2014.
Basilea press release, Apr. 7, 2014.
Basilea press release, Jun. 4, 2013.
Basilea press release, Sep. 6, 2016.
Berges et al., "Abstract A183: The novel tubulin-binding 'tumor checkpoint controller' BAL101553 exerts EB1 expression-dependent antitumor effects on glioblastoma stem-like cells in vitro and in vivo," AACR-NCI-EORTC International Conference: Molecular Targets and Cancer Therapeutics; Nov. 5-9, 2015.
Berges et al., "Abstract A183: The novel tubulin-binding 'tumor checkpoint controller' BAL101553 exerts EB1expression-dependent antitumor effects on glioblastoma stem-like cells in vitro and in vivo," AACR-NCI-EORTC International Conference: Molecular Targets and Cancer Therapeutics; Nov. 5-9, 2015. Poster.
Berges et al., "The Novel Tubulin-Binding Checkpoint Activator BAL101553 Inhibits EB1-Dependent Migration and Invasion and Promotes Differentiation of Glioblastoma Stem-like Cells," Mol Cancer Ther 2016, 15 (11), 2740-2749.
Bocci et al: "Pharmacokinetics of metronomic chemotherapy: a neglected but crucial aspect", Nature Reviews Clinical Oncology, vol. 13, No. 11, May 17, 2016 (May 17, 2016), pp. 659-673, XP055417627.
Breuleux et al., "BAL27862: A Unique Microtubule Destabilizer Active Against Chemorefractory Breast Cancers," Thirty-Second Annual CTRC-AACR San Antonio Breast Cancer Symposium—Dec. 10-13, 2009.
Breuleux et al., "BAL27862: A Unique Microtubule Destabilizer Active Against Chemorefractory Breast Cancers," Thirty-Second Annual CTRC-AACR San Antonio Breast Cancer Symposium—Dec. 10-13, 2009. (Poster).
Broggini-Tenzer et al., "Abstract A185: Combined treatment strategies for microtubule interfering agent-resistant tumors," AACR-NCI-EORTC International Conference: Molecular Targets and Cancer Therapeutics; Nov. 5-9, 2015.
Broggini-Tenzer et al., "The novel microtubule-destabilizing drug BAL101553 (prodrug of BAL27862) sensitizes a treatment refractory tumor model to radiation therapy," European Journal of Cancer 2014 50 SUPPL. 6 (65-66) (Poster).
Burger et al., "BAL101553 (prodrug of BAL27862): The 'Spindle Assembly Checkpoint' is required for anti-cancer activity," Cancer Research 2015 75:15 SUPPL. 1 (Poster).
Calvert et al: "A first-in human (FIH) dose-escalation study of the safety, pharmacokinetics (PK), and pharmacodynamics (PD) of intravenous BAL101553, a novel microtubule inhibitor, in adult patients with advanced solid tumors", Journal of Clinical Oncology; 2013 ASCO Annual Meeting, Amer Soc Clinical Oncology Journal of Clinical Oncology, American Society of Clinical Oncology, US vol. 31 (suppl.), No. 15 May 31, 2013 (May 31, 2013), pp. 1-2, XP002727516.
Calvert et al., "A first-in-human, dose escalation study of BAL101553, a novel microtubule inhibitor, in adult patients with advanced solid tumours," J Clin Oncol 31:15, 2013 (suppl 1; abstr 2566) (Poster).
Clinicaltrials.gov, "NCT02895360," Feb. 21, 2020.
Clinicaltrials.gov, "NCT02490800," Feb. 21, 2020.
Danel et al., "BAL27862, a novel microtubule-destabilizing drug binding to the colchicine site of tubulin with distinct effects on microtubule organization," 2014-EMBO Poster Abstract (Poster).
Duran et al., "Abstract C29: Elevated CDKN1A (p21) expression in human cancer cell variants selected for resistance to the novel microtubule depolymerizing agent BAL27862 (active moiety of BAL 101553)," Molecular Cancer Therapeutics 2011 10:11 SUPPL. 1.
Duran et al., "Abstract C29: Elevated CDKN1A (p21) expression in human cancer cell variants selected for resistance to the novel microtubule depolymerizing agent BAL27862 (active moiety of BAL 101553)," Molecular Cancer Therapeutics 2011 10:11 SUPPL. 1. (Poster).
Duran et al., "Abstract 4412: In vitro activity of the novel tubulin active agent BAL27862 in MDR1(+) and MDR1(−) human breast and ovarian cancer variants selected for resistance to taxanes," AACR 101st Annual Meeting 2010—Apr. 17-21, 2010.
Duran et al., "Abstract 4412: In vitro activity of the novel tubulin active agent BAL27862 in MDR1(+) and MDR1(−) human breast and ovarian cancer variants selected for resistance to taxanes," AACR 101st Annual Meeting 2010—Apr. 17-21, 2010. (Poster).
Esteve et al., "Abstract 1977: BAL27862: A unique microtubuletargeted drug that suppresses microtubule dynamics, severs microtubules, and overcomes Bcl-2- and tubulin subtype-related drug resistance," AACR 101st Annual Meeting 2010—Apr. 17-21, 2010. (Poster).
Esteve et al., "Abstract 1977: BAL27862: A unique microtubuletargeted drug that suppresses microtubule dynamics, severs microtubules, and overcomes Bcl-2- and tubulin subtype-related drug resistance," AACR 101st Annual Meeting 2010—Apr. 17-21, 2010.
Garces et al, "A phase I study to assess the safety, pharmacokinetics (PK), pharmacodynamics (PD) and antitumor activities of daily oral BAL101553, a novel tumor checkpoint controller (TCC) in adult

(56) References Cited

OTHER PUBLICATIONS patients with progressive or ecurrent glioblastoma (GBM) or high-grade glioma," J. Clin. Oncol. 2017 35:15, (Abstract), May 30, 2017.

* cited by examiner

DOSAGE PRINCIPLE FOR DRUGS USEFUL FOR TREATING NEOPLASTIC DISEASES

This application is a National Stage Application of PCT/EP2018/062601 filed May 15, 2018, which claims priority from European Patent Application No. 17171226.8, filed on May 16, 2017. The priority of said PCT and European Patent Application are claimed. Each of the prior mentioned applications is hereby incorporated by reference herein in its entirety.

The present invention relates to a new dosage principle for drugs useful for treating neoplastic diseases. More particular, the present invention relates to a new dosage regimen for the anti-cancer drug BAL27862 and pro-drugs thereof, in particular BAL101553 and pharmaceutically acceptable salts of said drug and pro-drugs.

Microtubules are one of the components of the cell cytoskeleton and are composed of heterodimers of alpha and beta tubulin. Agents that target microtubules are among the most effective cytotoxic chemotherapeutic agents having a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukemia and lymphoma, as well as solid tumors, such as lung cancer. Microtubule stabilising agents (e.g. the taxanes such as paclitaxel, docetaxel) are used for example in the treatment of solid tumors, including breast, lung and prostate cancer.

WO2004/103994 describes a recently discovered class of microtubule destabilising agents. One compound falling within this class, known as BAL27862 (referred to herein as the compound of formula I-A), and shown in WO2004/103994 under Example 58, has the structure and chemical name given below:

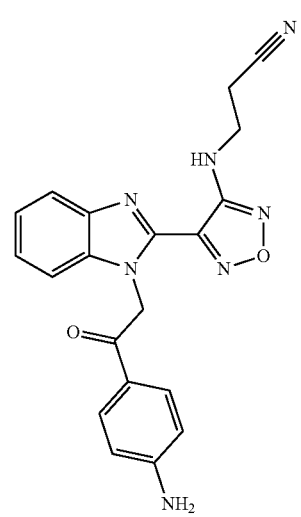

(I-A)

3-(4-{1-[2-(4-Amino-phenyl)-2-oxo-ethyl]-1H-benzoimidazol-2-yl}-furazan-3-ylamino)-propionitrile.

WO2011/012577 discloses pro-drugs of the compounds disclosed in WO2004/103994. One compound known as BAL101553 (referred to herein as the compound of formula I-B) and shown in WO2011/012577 under Example 1 has the chemical name and structure given below:

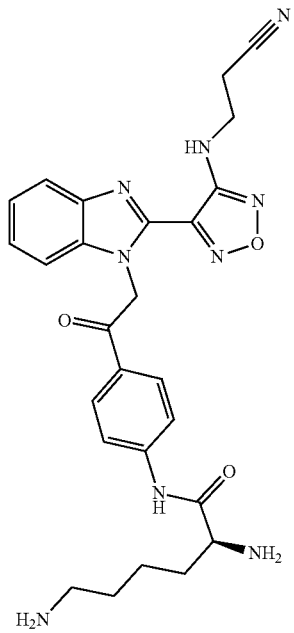

(I-B)

(S)-2,6-Diamino-hexanoic acid [4-(2-{2-[4-(2-cyano-ethylamino)-furazan-3-yl]-benzoimidazol-1-yl}-acetyl)-phenyl]-amide.

The compound of formula I-B is a highly water-soluble pro-drug of the compound of formula I-A which forms the compound of formula I-A in-vivo following administration. The compound of formula I-B is particularly advantageously used in the form of a pharmaceutically acceptable acid addition salt, like a hydrochloride salt thereof, in particular in the form of its dihydrochloride salt. These compounds have been shown to arrest tumor cell proliferation and induce apoptosis. The compound of formula I-A and the pro-drug of formula I-B have demonstrated antitumor activity across a broad panel of experimental tumor models.

WO2015/173341 describes a dosage regime in which compounds of formula I and pharmaceutically acceptable derivatives thereof as described therein are administered to patients intravenously at a specific dosage frequency and a specific treatment cycle at a dose being below the maximum tolerated dose defined for said dosage frequency and treatment cycle, but providing at least the same exposure of the tissue of the cancer from which said cancer patient is suffering, to said drug as provided by the maximum tolerated dose (MTD) at the same dosage frequency and treatment cycle. This was based on the belief that intravenous doses significantly below the MTD (sub-MTD doses) could provide an exposure of the tumor tissue to the drug, which is substantially the same or even better than the exposure achievable by intravenous administration of the MTD. The Examples describe the phase I escalation study in which 60 mg/m$^2$ of the compound of formula I-B was defined as the MTD for 2-hour intravenous administration.

The phase ½a trial results of the compound of formula I-B were presented at the ASCO Annual Meeting Jun. 3-7, 2016 in a poster entitled "Phase1/2a trial of intravenous BAL101553, a novel tumor checkpoint controller in advanced solid tumors" (2016-ASCO Poster Abstract 2525). In the trial the compound of formula I-B was administered to patients by 2-hour infusion on study days 1, 8 and 15, q28 days. In view of observations of asymptomatic myocardial ischemia a recommended phase 2 dose of 30 mg/m$^2$ was defined. The poster also reported dose-dependent vascular effects that were dose-limiting and related to peak drug concentration ($C_{max}$). In view of these findings alternative strategies to optimize tumor drug exposure and the therapeutic window are warranted.

A poster entitled "The novel tubulin-binding "tumor checkpoint controller" BAL101553 has differential effects on tumor vascularization with i.v. and oral dosing and provides superior anti-tumor activity in combination with bevacizumab" was presented to the AACR (Abstract No. LB-151) on 30 Apr. 2017. This discloses that phase ½a clinical trials are being performed with both oral daily and i.v. BAL101553, including 2 hour i.v. infusion, 48 hour i.v. infusion.

The present invention relates in a first aspect to a compound of formula I

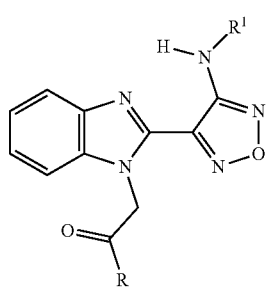

(I)

wherein
R represents phenyl or pyridinyl;
wherein phenyl is optionally substituted by one or two substituents independently selected from lower alkyl, lower alkoxy, hydroxyl, amino, lower alkylamino, lower dialkylamino, acetylamino, halogen and nitro, preferably selected from lower alkyl, lower alkoxy, amino, acetylamino, halogen and nitro; and wherein pyridinyl is optionally substituted by amino or halogen;
$R^1$ represents hydrogen or cyano-lower alkyl;
and wherein the prefix lower denotes a radical having up to and including a maximum of 4 carbon atoms; or a pharmaceutically acceptable derivative thereof, which pharmaceutically acceptable derivative may be the dihydrochloride salt of the compound of formula I-B

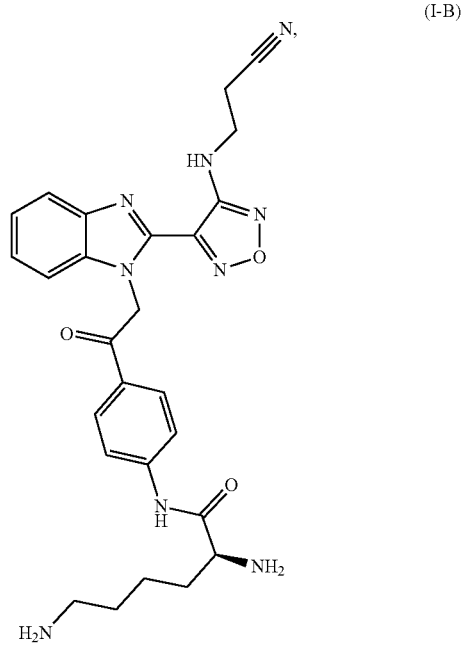 [SMILES: N#CCCNc1nonc1-c1nc2ccccc2n1CC(=O)c1ccc(NC(=O)[C@@H](N)CCCCN)cc1]

(I-B)

for use in the treatment of a neoplastic disease in a patient, wherein said compound or pharmaceutically acceptable derivative thereof is intravenously administered to said patient, preferably by continuous infusion, over a period of at least about 8 hours, and wherein the dose of the compound of formula I or pharmaceutically acceptable derivative thereof is at least the molar equivalent of about 45 mg/m² of the dihydrochloride salt of the compound formula I-B.

In a further aspect the invention provides use of a compound of formula I or pharmaceutically acceptable derivative thereof, which pharmaceutically acceptable derivative may be the dihydrochloride salt of the compound of formula I-B, in the manufacture of a medicament for the treatment of a neoplastic disease in a patient, wherein said compound or pharmaceutically acceptable derivative thereof is intravenously administered to said patient, preferably by continuous infusion, over a period of at least about 8 hours, and wherein the dose of the compound of formula I or pharmaceutically acceptable derivative thereof is at least the molar equivalent of about 45 mg/m² of the dihydrochloride salt of the compound of formula I-B.

In a further aspect the invention provides a method of treating a neoplastic disease in a patient comprising administering to said patient a compound of formula I or pharmaceutically acceptable derivative thereof, which pharmaceutically acceptable derivative may be the dihydrochloride salt of the compound of formula I-B, wherein said compound or pharmaceutically acceptable derivative thereof is intravenously administered to said patient, preferably by continuous infusion, over a period of at least about 8 hours, and wherein the dose of the compound of formula I or pharmaceutically acceptable derivative thereof is at least the molar equivalent of about 45 mg/m² of the dihydrochloride salt of the compound of formula I-B.

Additional aspects and embodiments of the invention are described in more detail below.

Figure 1:
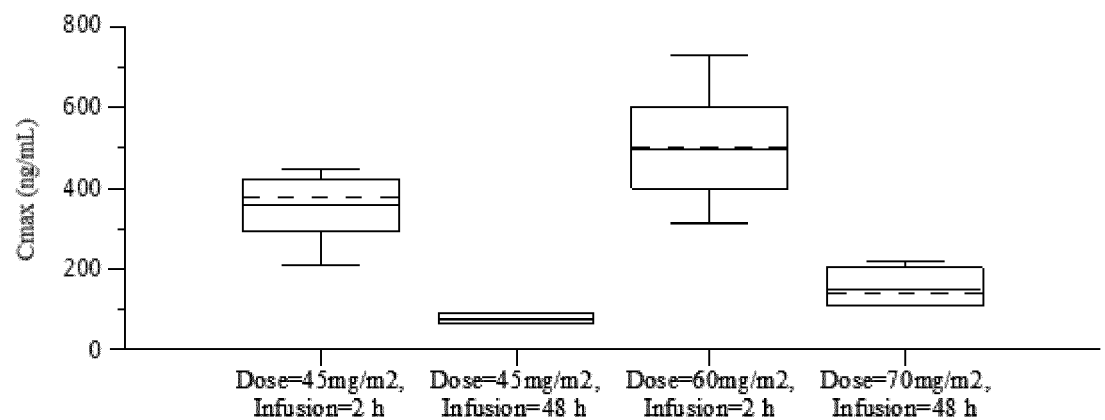
FIG. 1 shows the $C_{max}$ results of BAL27862 from patients administered with the dihydrochloride salt of BAL101553 as a 2-hour intravenous infusion and patients administered with the dihydrochloride salt of BAL101553 as a 48-hour intravenous infusion. In the box and whiskers plots the box represents 25th and 75th percentiles (interquartile range, IQR), inside the box the solid line is the arithmetic mean and the dashed line is the median; the whiskers represent 1.5× IQR or min/max range; individual data points outside the IQR whiskers are shown as individual dot outliers.

Preferred compounds of formula I include those wherein R and R¹ are defined as follows:

| R | R¹ |
|---|---|
| 4-Cl-phenyl | H |
| 4-MeO-phenyl | H |
| 3-MeO-phenyl | H |
| 4-Br-phenyl | H |
| 2,4-diCl-phenyl | H |
| 2-Cl-phenyl | H |
| 3-Cl-phenyl | H |
| 4-Et₂N-phenyl | H |
| 4-Me-phenyl | H |
| 4-Br-phenyl | CH₂CH₂CN |
| 4-MeO-phenyl | CH₂CH₂CN |
| 4-O₂N-phenyl | H |
| 4-H₂N-phenyl | H |
| 2,3-diMe-phenyl | H |
| 2,3-diMe-phenyl | CH₂CH₂CN |
| 4-Et-phenyl | H |
| 4-Et-phenyl | CH₂CH₂CN |
| 4-O₂N-phenyl | CH₂CH₂CN |
| 4-H₂N-phenyl | CH₂CH₂CN |
| 2-pyridyl | H |

| R | R¹ |
|---|---|
| 4-(AcNH)-phenyl | H |
| 2-(O₂N), 4-(AcNH)-phenyl | H |
| 2-(O₂N), 4-(H₂N)-phenyl | H |
| 2-(O₂N), 4-(Cl)-phenyl | H |
| 4-F-phenyl | H |
| 2-(O₂N), 4-(MeO)-phenyl | H |
| 2-(H₂N), 4-(MeO)-phenyl | CH₂CH₂CN |
| 6-Cl-pyridin-3-yl | H |
| 2,5-di-F-phenyl | H |
| 2-MeO, 4-HO-phenyl | H |
| 2-MeO, 4-MeO-phenyl | H |
| 6-(H₂N)-pyridin-3-yl | H |
| 6-(H₂N)-pyridin-3-yl | CH₂CH₂CN |
| 3,4-di-HO-phenyl | H | or pharmaceutically acceptable derivatives thereof.

Especially preferred are compounds wherein R and R¹ are defined as follows:

| R | R¹ |
|---|---|
| 4-(H₂N)-phenyl | H |
| 4-(H₂N)-phenyl | CH₂CH₂CN |
| 6-(H₂N)-pyridin-3-yl | H |
| 6-(H₂N)-pyridin-3-yl | CH₂CH₂CN | or pharmaceutically acceptable derivatives thereof.

An especially preferred compound is the compound of formula I-A or pharmaceutically acceptable derivative thereof:

(I-A)

The term derivative or derivatives in the phrase "pharmaceutically acceptable derivative" or "pharmaceutically acceptable derivatives" of compounds of formula I relates to pharmaceutically acceptable salts, pro-drugs and pharmaceutically acceptable salts of pro-drugs thereof.

Reference to compounds of formula I and pharmaceutically acceptable derivatives thereof includes solvates and complexes (including hydrates) thereof as well as any polymorphs of the foregoing. Reference to compounds of formula I and pharmaceutically acceptable derivatives thereof also includes all optical, geometric and tautomeric isomers where possible.

Salts are preferably acid addition salts. Salts are formed, preferably with organic or inorganic acids, from compounds of formula I or pharmaceutically acceptable derivatives thereof with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound according to the invention may be administered in the form of a pro-drug, including pharmaceutically acceptable salts thereof, which is broken down in the human to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula I. Pro-drug amides are formed from the amino function of the amino acid or the N terminal of the peptide and suitable carboxy group(s) in the compound of formula I, or from the acid function of the amino acid or the C terminal of the peptide and suitable amino group(s) in the compound of formula I. Particularly preferably the pro-drug amides are formed from the amino group(s) present within the R group of formula I. More preferably, the pro-drug is an amide formed from an amino group present within the R group of the compound of formula I as defined above and the carboxy group of glycine, alanine or lysine.

Even more preferably the compound of formula I is in the form of a pro-drug selected from the compounds of the following formulae and pharmaceutically acceptable salts thereof:

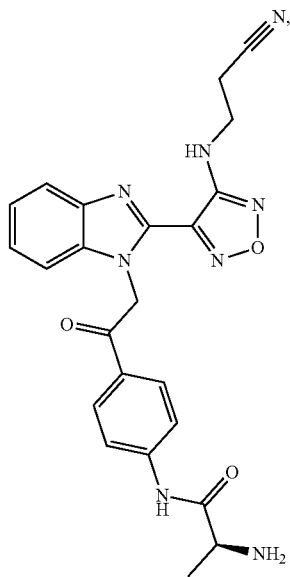

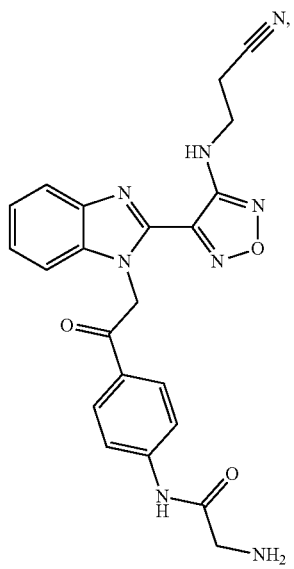

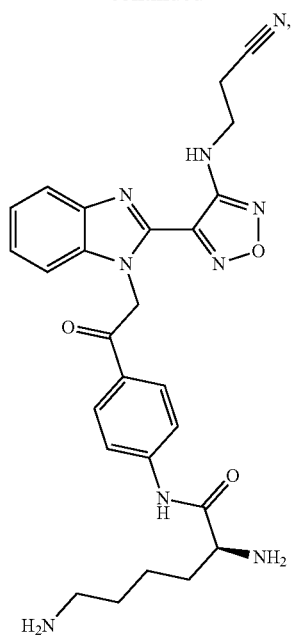
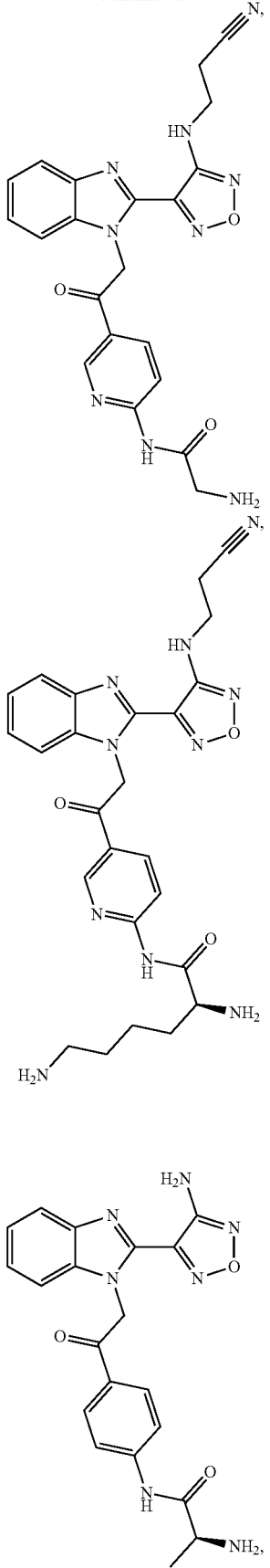

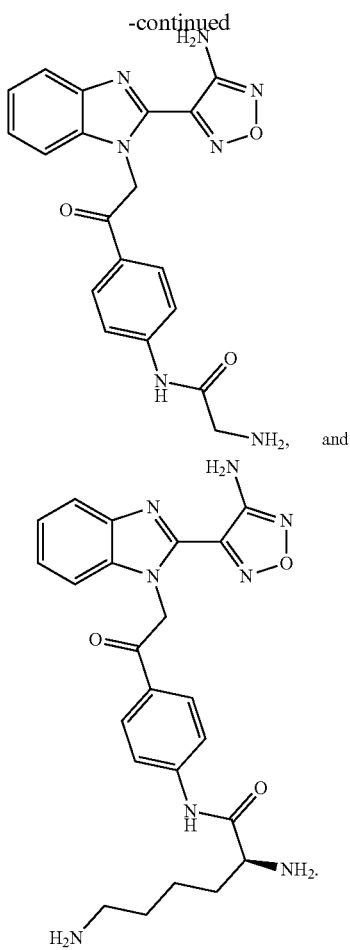

In an especially preferred embodiment the compound of formula I according to the invention is a pro-drug of the compound of formula I-A, preferably in the form of the pro-drug of the compound of formula I-B:

(I-B)

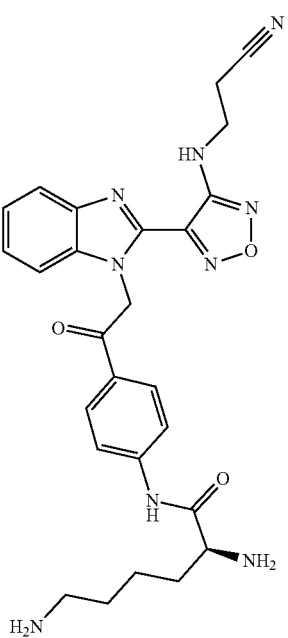

or a pharmaceutically acceptable salt thereof, preferably a hydrochloride salt, most preferably a dihydrochloride salt.

The pro-drugs of the invention may be prepared as described for example in WO2012/098207 on pages 40 to 42, which are hereby incorporated by reference.

The dihydrochloride salt of the compound of formula I-B is administered at a dosage level of at least about 45 mg/m$^2$. In other embodiments of the invention higher dosage levels are used. For example the dosage level of the dihydrochloride salt of the compound of formula I-B may be at least about 60 mg/m$^2$, at least about 70 mg/m$^2$, at least about 100 mg/m$^2$, or even at least about 140 mg/m$^2$. In some cases the dosage level of the dihydrochloride salt of compound of formula I-B may be about 200 mg/m$^2$. Examples of ranges of dosage levels of the dihydrochloride salt of compound of formula I-B include about 45 mg/m$^2$ to about 200 mg/m$^2$, about 70 mg/m$^2$ to about 200 mg/m$^2$, about 45 mg/m$^2$ to about 140 mg/m$^2$, about 70 mg/m$^2$ to about 140 mg/m$^2$, about 45 mg/m$^2$ to about 100 mg/m$^2$, or about 70 mg/m$^2$ to about 100 mg/m$^2$. The dosage level of the dihydrochloride salt of the compound of formula I-B may be up to about 60 mg/m$^2$, up to about 70 mg/m$^2$, up to about 100 mg/m$^2$, up to about 140 mg/m$^2$ or up to about 200 mg/m$^2$.

The compound of formula I or pharmaceutically acceptable derivative thereof is administered at the molar equivalents of the given dosage amounts for the dihydrochloride salt of the compound of formula I-B.

The molar mass of the dihydrochloride salt of the compound of formula I-B is 588.49 g/mol ($C_{26}H_{29}N_9O_3 \times 2HCl$) based on IUPAC2009 atomic weights. The compound of formula I-B has the CAS registry number 1387574-54-0. Converting the above dosage amounts for the dihydrochloride salt of the compound of formula I-B into molar amounts, the compound of formula I or pharmaceutically acceptable derivative thereof is administered at a dosage level of at least about 0.076 moles/m$^2$. In other embodiments of the invention higher dosage levels are used. For example the dosage level may be at least about 0.102 moles/m$^2$, at least about 0.119 moles/m$^2$, at least about 0.170 moles/m$^2$, or even at least about 0.238 moles/m$^2$. In some cases the dosage level may be about 0.340 moles/m$^2$. Examples of ranges of dosage levels include about 0.076 moles/m$^2$ to about 0.340 moles/m$^2$, about 0.119 moles/m$^2$ to about 0.340 moles/m$^2$, about 0.076 moles/m$^2$ to about 0.238 moles/m$^2$, about 0.119 moles/m$^2$ to about 0.238 moles/m$^2$, about 0.076 moles/m$^2$ to about 0.170 moles/m$^2$, or about 0.119 moles/m$^2$ to about 0.170 moles/m$^2$. The dosage level of the dihydrochloride salt of the compound of formula I-B may be up to about up to about 0.102 moles/m$^2$, up to about 0.119 moles/m$^2$, up to about 0.170 moles/m$^2$, up to about 0.238 moles/m$^2$ or up to about 0.340 moles/m$^2$.

Dosages of the dihydrochloride salt of the compound of formula I-B may be expressed in terms of amounts of the free base of the compound of formula I-B. The molar mass of the free base of the compound of formula I-B is 515.58 g/mol. Thus 45 mg/m$^2$ of the dihydrochloride salt of the compound of formula I-B is approximately equal to 39.4 mg/m$^2$ of the free base of the compound of formula I-B. 60 mg/m$^2$ of the dihydrochloride salt of the compound of formula I-B is approximately equal to 52.6 mg/m$^2$ of the free base of the compound of formula I-B. 70 mg/m$^2$ of the dihydrochloride salt of the compound of formula I-B is approximately equal to 61.3 mg/m$^2$ of the free base of the compound of formula I-B. 100 mg/m$^2$ of the dihydrochloride salt of the compound of formula I-B is approximately equal to 87.6 mg/m$^2$ of the free base of the compound of formula I-B. 140 mg/m$^2$ of the dihydrochloride salt of the compound of formula I-B is approximately equal to 122.7 mg/m² of the free base of the compound of formula I-B. 200 mg/m² of the dihydrochloride salt of the compound of formula I-B is approximately equal to 175.2 mg/m² of the free base of the compound of formula I-B.

Dosages of the dihydrochloride salt of the compound of formula I-B may be expressed in terms of amounts of the free base of the compound of formula I-A. The molar mass of the free base of the compound of formula I-A is 387.40 g/mol. Thus 45 mg/m² of the dihydrochloride salt of the compound of formula I-B is approximately equal to 29.6 mg/m² of the free base of the compound of formula I-A. 60 mg/m² of the dihydrochloride salt of the compound of formula I-B is approximately equal to 39.5 mg/m² of the free base of the compound of formula I-A. 70 mg/m² of the dihydrochloride salt of the compound of formula I-B is approximately equal to 46.1 mg/m² of the free base of the compound of formula I-A. 100 mg/m² of the dihydrochloride salt of the compound of formula I-B is approximately equal to 65.8 mg/m² of the free base of the compound of formula I-A. 140 mg/m² of the dihydrochloride salt of the compound of formula I-B is approximately equal to 92.2 mg/m² of the free base of the compound of formula I-A. 200 mg/m² of the dihydrochloride salt of the compound of formula I-B is approximately equal to 131.7 mg/m² of the free base of the compound of formula I-A.

In each case the indicated surface area represents the body surface area (BSA), which can be determined by methods generally known in the art, e.g. by measurement or calculation. Doses for chemotherapy treatment are usually calculated according to BSA, which is determined by using a nomogram scale or by using a BSA calculator. Once the BSA is determined, it is multiplied by the amount of drug specified in the regimen to give the total dose of drug to be administered (Chu and DeVita, Physicians' Cancer Chemotherapy Drug Manual 2013, Jones & Bartlett Learning). According to the Washington Manual of Oncology the DuBois formula is the most widely accepted nomogram for calculating BSA and is considered the "gold standard" for BSA calculations. The formula is given as $BSA(m^2)=W^{0.425}*H^{0.725}*0.007184$, where W is weight in kg and H is height in cm (Govindan and Morgensztern, Washington Manual of Oncology). In a study of cancer patients in the UK, the mean BSA for men was found to be 1.91 m² (1.90-1.92 95% confidence interval) and the mean BSA for women was found to be 1.71 m² (1.70-1.72 95% confidence interval) (Sacco et al., 2010, PLoS ONE 5(1): e8933. doi:10.1371/journal.pone.0008933).

Based on the findings of Sacco et al. a dose of 45 mg/m² for men would typically require a dose of about 86 mg. A dose of 70 mg/m² for men would typically require a dose of about 134 mg. A dose of 140 mg/m² for men would typically require a dose of about 267 mg. Likewise a dose of 45 mg/m² for women would typically require a dose of about 77 mg. A dose of 70 mg/m² for women would typically require a dose of about 120 mg. A dose of 140 mg/m² for women would typically require a dose of about 239 mg.

The dose of the compound of formula I or derivative thereof, which derivative may be the compound of formula I-B, is administered over a period of at least about 8 hours, preferably over a period of at least about 24 hours, more preferably over a period of at least about 48 hours. In some cases the administration may be over a period of about 120 hours. Examples of ranges of administration periods include about 8 to about 120 hours, about 24 hours to about 120 hours, about 48 hours to about 120 hours, about 24 hours to about 64 hours, or about 48 hours to about 64 hours. In one embodiment the dose is administered over a period of about 48 hours.

The compound of formula I or pharmaceutically acceptable derivative thereof is administered intravenously over a prescribed period of time, suitably continuously and preferably substantially without interruption, e.g. the period of administration does not include an interruption of more than 30 minutes and/or a cumulative interruption of more than 10% of the total of period of administration. Preferably the compound of formula I or pharmaceutically acceptable derivative thereof is administered by continuous infusion. Administration by continuous infusion involves intravenous administration of the medication without interruption over the prescribed period of time. This can mean that the rate of infusion does not vary by more than 50% from the mean flow rate over the duration of administration. The administration is usually by means of a pump which provides the patient with intravenous administration of the medicament at a generally constant rate. Suitable devices are well-known in the art and may be mechanical or electrical. Generally the devices are portable by the patient and can be worn by the patient, e.g. to provide minimal interference in daily life. In other words, the pump may be attachable to the patient's body e.g. via a cannula. An administration tube or other conduit connects the pump to the infusion site on the patient's body. The elastomeric infusion pump is one type of mechanical device, which comprises an elastomeric reservoir in which the solution to be administered is placed, and a flow restrictor system located in the administration tube. The combination of both the pressure generated by the filled reservoir and the flow restrictor provides a constant flow rate, independently of gravity. Alternative, non-electronic devices are pumps using a spring (e.g. a coil shaped spring). Electronic pumps are also in use and generally utilize syringes or cartridges as reservoirs for the infusion solution that is administered to the patient. Thiveaud et al., European Journal of Hospital Pharmacy Practice, P 2/2005 compare the performance of some elastomeric devices. Although any type of infusion pump may be used in connection with the present invention, elastomeric pumps are preferred as they are generally smaller and less obtrusive than electrical pumps.

Preferably the dose of the compound of formula I or derivative thereof, which derivative may be the compound of formula I-B, is administered by continuous infusion over a period of at least about 24 hours, preferably over a period of at least about 48 hours. In some cases the administration by continuous infusion may be over a period of about 120 hours. Examples of ranges of administration periods for continuous infusion include about 24 hours to about 120 hours, about 48 hours to about 120 hours, about 24 hours to about 64 hours, or about 48 hours to about 64 hours. In one embodiment the dose is administered by continuous infusion over a period of about 48 hours.

The compound of formula I or derivative thereof, which may be the dihydrochloride salt of the compound of formula I-B, is administered according to a desired treatment cycle. In such a cycle the compound of formula I or derivative thereof will usually be administered at least once per week. Optionally there may be an administration pause every fourth week, e.g. such that the patient receives treatment every week for three weeks and then no treatment in the fourth week. For doses of longer duration e.g. more than 64 hours, such as 120 hours, the treatment cycle may be once every two weeks or once every three weeks. Thus example treatment cycles include the following:

For 24-hour administration/28 day treatment cycle: administration on days 1, 8, 15 (three administrations).

For 24-hour administration/28 day treatment cycle: administration on days 1, 8, 15, 22 (four administrations).

For 48-hour administration/28 day treatment cycle: administration on days 1, 8, 15 (three administrations).

For 48-hour administration/28 day treatment cycle: administration on days 1, 8, 15, 22 (four administrations).

For 64-hour administration/28 day treatment cycle: administration on days 1, 8, 15 (three administrations).

For 64-hour administration/28 day treatment cycle: administration on days 1, 8, 15, 22 (four administrations).

For 64 hour administration/28 day treatment cycle: administration on days 1 and 15 (two administrations).

For 64-hour administration/42 day treatment cycle: administration on days 1 and 22 (two administrations).

For 120-hour administration/28 day treatment cycle: administration on days 1 and 15 (two administrations).

For 120-hour administration/42 day treatment cycle: administration on days 1 and 22 (two administrations).

In the above description of treatment cycles, "administration on day X" means that administration commences on day X.

For intravenous application, the active ingredient can be in powder (e.g. lyophilized) form and reconstituted with a suitable diluent e.g. saline solution or Ringer lactate solution, preferably Ringer lactate solution, immediately prior to administration. The active ingredient may be initially reconstituted with saline solution or Ringer lactate solution and then diluted to the required concentration with Ringer lactate solution.

The dosage volume can be for example from about 100 ml to about 1000 ml, e.g. at least about 100 ml, e.g. up to about 1000 ml. Preferably the dosage volume is from about 100 ml to about 500 ml, e.g. at least about 100 ml, e.g. up to about 500 ml. Other examples of dosage volumes are about 200 ml to about 500 ml, e.g. at least 200 ml, e.g. up to 500 ml. In one embodiment the dosage volume is about 240 ml.

Depending on solubility of the compound of formula I or pharmaceutical derivative thereof it may be desirable to use larger volumes with higher doses. Smaller volumes may require lower flow rates which may lead to inconsistencies in dosing as variability in the flow rate will lead to higher variability in dosing. For example we have found that a more reliable flow rate can be achieved with a volume of 240 ml rather than 120 ml over 48 hours. On the other hand we have also found that care needs to be taken with regard to the relative level of residual environmental impurities, which may become an issue when the concentration of active ingredient is low.

The flow rate is determined by the dosage volume and the time period over which the dosage is administered. For example the flow rate may be about 1 ml/hour to about 12 ml/hour, e.g. 2.5 ml/hour to about 12 ml/hour, e.g. about 2.5 ml/hour to about 10 ml/hour. The flow rate may be at least about 1 ml/hour, e.g. at least about 2.5 ml/hour, e.g. up to 12 ml/hour, e.g. up to 10 ml/hour, e.g. less than 12 ml/hour, e.g. less than 10 ml/hour. A typical flow rate is about 5 ml/hour.

In one embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient over a period of at least about 24 hours, and wherein the dose of the compound of formula I or pharmaceutically acceptable derivative thereof is at least the molar equivalent of about 45 mg/m$^2$ of the dihydrochloride salt of the compound formula I-B.

In another embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient by continuous infusion over a period of at least about 24 hours, and wherein the dose of the compound of formula I or pharmaceutically acceptable derivative thereof is at least the molar equivalent of about 45 mg/m$^2$ of the dihydrochloride salt of the compound formula I-B.

In another embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient by continuous infusion over a period of at least about 24 hours, and wherein the dose of the compound of formula I or pharmaceutically acceptable derivative thereof is at least the molar equivalent of about 60 mg/m$^2$ of the dihydrochloride salt of the compound formula I-B.

In another embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient by continuous infusion over a period of at least about 48 hours, and wherein the dose of the compound of formula I or pharmaceutically acceptable derivative thereof is at least the molar equivalent of about 60 mg/m$^2$ of the dihydrochloride salt of the compound formula I-B.

In another embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient by continuous infusion over a period of at least about 24 hours, and wherein the dose of the compound of formula I or pharmaceutically acceptable derivative thereof is at least the molar equivalent of about 70 mg/m$^2$ of the dihydrochloride salt of the compound formula I-B.

In another embodiment the invention provides a compound of formula I or pharmaceutically acceptable derivative thereof, which pharmaceutically acceptable derivative may be the dihydrochloride salt of the compound of formula I-B, for use in the treatment of a neoplastic disease in a patient, wherein said compound or pharmaceutically acceptable derivative thereof is intravenously administered to said patient by continuous infusion over a period of at least about 48 hours, and wherein the dose of the compound of formula I or pharmaceutically acceptable derivative thereof is at least the molar equivalent of about 70 mg/m$^2$ of the dihydrochloride salt of the compound formula I-B.

In another embodiment the compound of formula I-B or pharmaceutically acceptable salt thereof, preferably the dihydrochloride salt of the compound of formula I-B, is administered to the patient over a period of at least about 8 hours and wherein the dose of the compound of formula I-B or pharmaceutically acceptable salt thereof is at least the molar equivalent of about 45 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of at least about 24 hours and wherein the dose of the compound of formula I-B or pharmaceutically acceptable salt thereof is at least the molar equivalent of about 45 mg/m² of the dihydrochloride salt of the compound formula I-B.

In another embodiment the compound of formula I-B, or pharmaceutically acceptable salt thereof, preferably the dihydrochloride salt of the compound of formula I-B, is administered to the patient by continuous infusion over a period of at least about 24 hours and wherein the dose of the compound of formula I-B or pharmaceutically acceptable salt thereof is at least the molar equivalent of about 60 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of at least about 24 hours and wherein the dose of the compound of formula I-B or pharmaceutically acceptable salt thereof is at least the molar equivalent of about 70 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of at least about 48 hours and wherein the dose of the compound of formula I-B or pharmaceutically acceptable salt thereof is at least the molar equivalent of about 45 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of at least about 48 hours and wherein the dose of the compound of formula I-B or pharmaceutically acceptable salt thereof is at least the molar equivalent of about 60 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of at least about 48 hours and wherein the dose of the compound of formula I-B or pharmaceutically acceptable salt thereof is at least the molar equivalent of about 70 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of about 64 hours and wherein the dose of the compound of formula I-B or pharmaceutically acceptable salt thereof is at least the molar equivalent of about 45 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of about 64 hours and wherein the dose of the compound of formula I-B or pharmaceutically acceptable salt thereof is at least the molar equivalent of about 60 mg/m² of the dihydrochloride salt of the compound formula I-B.

In another embodiment the compound of formula I-B or pharmaceutically acceptable salt thereof, preferably the dihydrochloride salt of the compound of formula I-B, is administered to the patient by continuous infusion over a period of about 64 hours and wherein the dose of the compound of formula I-B or pharmaceutically acceptable salt thereof is at least the molar equivalent of about 70 mg/m². of the dihydrochloride salt of the compound formula I-B.

Additional embodiments of the invention are shown in Table A below:

TABLE A

| Embodiment | Compound | Dose (mg/m2) | Administration period (hours) | Volume (ml) |
|---|---|---|---|---|
| 1 | I-A* | 45 | 24 | 100 |
| 2 | I-A* | 45 | 24 | 200 |
| 3 | I-A* | 45 | 24 | 500 |
| 4 | I-A* | 45 | 48 | 100 |
| 5 | I-A* | 45 | 48 | 200 |
| 6 | I-A* | 45 | 48 | 500 |
| 7 | I-A* | 45 | 64 | 100 |
| 8 | I-A* | 45 | 64 | 200 |
| 9 | I-A* | 45 | 64 | 500 |
| 10 | I-A* | 45 | 120 | 100 |
| 11 | I-A* | 45 | 120 | 200 |
| 12 | I-A* | 45 | 120 | 500 |
| 13 | I-A* | 60 | 24 | 100 |
| 14 | I-A* | 60 | 24 | 200 |
| 15 | I-A* | 60 | 24 | 500 |
| 16 | I-A* | 60 | 48 | 100 |
| 17 | I-A* | 60 | 48 | 200 |
| 18 | I-A* | 60 | 48 | 500 |
| 19 | I-A* | 60 | 64 | 100 |
| 20 | I-A* | 60 | 64 | 200 |
| 21 | I-A* | 60 | 64 | 500 |
| 22 | I-A* | 60 | 120 | 100 |
| 23 | I-A* | 60 | 120 | 200 |
| 24 | I-A* | 60 | 120 | 500 |
| 25 | I-A* | 70 | 24 | 100 |
| 26 | I-A* | 70 | 24 | 200 |
| 27 | I-A* | 70 | 24 | 500 |
| 28 | I-A* | 70 | 48 | 100 |
| 29 | I-A* | 70 | 48 | 200 |
| 30 | I-A* | 70 | 48 | 500 |
| 31 | I-A* | 70 | 64 | 100 |
| 32 | I-A* | 70 | 64 | 200 |
| 33 | I-A* | 70 | 64 | 500 |
| 34 | I-A* | 70 | 120 | 100 |
| 35 | I-A* | 70 | 120 | 200 |
| 36 | I-A* | 70 | 120 | 500 |
| 37 | I-A* | 140 | 24 | 100 |
| 38 | I-A* | 140 | 24 | 200 |
| 39 | I-A* | 140 | 24 | 500 |
| 40 | I-A* | 140 | 48 | 100 |
| 41 | I-A* | 140 | 48 | 200 |
| 42 | I-A* | 140 | 48 | 500 |
| 43 | I-A* | 140 | 64 | 100 |
| 44 | I-A* | 140 | 64 | 200 |
| 45 | I-A* | 140 | 64 | 500 |
| 46 | I-A* | 140 | 120 | 100 |
| 47 | I-A* | 140 | 120 | 200 |
| 48 | I-A* | 140 | 120 | 500 |
| 49 | I-B* | 45 | 24 | 100 |
| 50 | I-B* | 45 | 24 | 200 |
| 51 | I-B* | 45 | 24 | 500 |

TABLE A-continued

| Embodiment | Compound | Dose (mg/m2) | Administration period (hours) | Volume (ml) |
|---|---|---|---|---|
| 52 | I-B* | 45 | 48 | 100 |
| 53 | I-B* | 45 | 48 | 200 |
| 54 | I-B* | 45 | 48 | 500 |
| 55 | I-B* | 45 | 64 | 100 |
| 56 | I-B* | 45 | 64 | 200 |
| 57 | I-B* | 45 | 64 | 500 |
| 58 | I-B* | 45 | 120 | 100 |
| 59 | I-B* | 45 | 120 | 200 |
| 60 | I-B* | 45 | 120 | 500 |
| 61 | I-B* | 60 | 24 | 100 |
| 62 | I-B* | 60 | 24 | 200 |
| 63 | I-B* | 60 | 24 | 500 |
| 64 | I-B* | 60 | 48 | 100 |
| 65 | I-B* | 60 | 48 | 200 |
| 66 | I-B* | 60 | 48 | 500 |
| 67 | I-B* | 60 | 64 | 100 |
| 68 | I-B* | 60 | 64 | 200 |
| 69 | I-B* | 60 | 64 | 500 |
| 70 | I-B* | 60 | 120 | 100 |
| 71 | I-B* | 60 | 120 | 200 |
| 72 | I-B* | 60 | 120 | 500 |
| 73 | I-B* | 70 | 24 | 100 |
| 74 | I-B* | 70 | 24 | 200 |
| 75 | I-B* | 70 | 24 | 500 |
| 76 | I-B* | 70 | 48 | 100 |
| 77 | I-B* | 70 | 48 | 200 |
| 78 | I-B* | 70 | 48 | 500 |
| 79 | I-B* | 70 | 64 | 100 |
| 80 | I-B* | 70 | 64 | 200 |
| 81 | I-B* | 70 | 64 | 500 |
| 82 | I-B* | 70 | 120 | 100 |
| 83 | I-B* | 70 | 120 | 200 |
| 84 | I-B* | 70 | 120 | 500 |
| 85 | I-B* | 140 | 24 | 100 |
| 86 | I-B* | 140 | 24 | 200 |
| 87 | I-B* | 140 | 24 | 500 |
| 88 | I-B* | 140 | 48 | 100 |
| 89 | I-B* | 140 | 48 | 200 |
| 90 | I-B* | 140 | 48 | 500 |
| 91 | I-B* | 140 | 64 | 100 |
| 92 | I-B* | 140 | 64 | 200 |
| 93 | I-B* | 140 | 64 | 500 |
| 94 | I-B* | 140 | 120 | 100 |
| 95 | I-B* | 140 | 120 | 200 |
| 96 | I-B* | 140 | 120 | 500 |

IA* means the compound of formula I-A or pharmaceutically acceptable derivative thereof
IB* means the compound of formula I-B or pharmaceutically acceptable salt thereof The embodiments in Table A are interpreted as illustrated below for embodiments 1 and 49: Embodiment 1 provides the compound of formula I-A or pharmaceutical derivative thereof for use in the treatment of a neoplastic disease in a patient, wherein said compound or pharmaceutically acceptable derivative thereof is intravenously administered to said patient by continuous infusion over a period of about 24 hours, wherein the dose of the compound of formula I-A or pharmaceutically acceptable derivative thereof is at least the molar equivalent of about 45 mg/m² of the dihydrochloride salt of the compound of formula I-B and wherein the dosage volume is about 100 ml.

Embodiment 49 provides the compound of formula I-B or pharmaceutically acceptable salt thereof, preferably the dihydrochloride salt thereof, for use in the treatment of a neoplastic disease in a patient, wherein said compound of formula I-B or pharmaceutically acceptable salt thereof is intravenously administered to said patient by continuous infusion over a period of about 24 hours, wherein the dose of the compound of formula I-B or pharmaceutically acceptable salt thereof is at least the molar equivalent of about 45 mg/m² of the dihydrochloride salt of the compound of formula I-B and wherein the dosage volume is about 100 ml.

During administration of the compound of formula I or pharmaceutically acceptable derivative thereof the mean increase in systolic blood pressure during administration compared to systolic blood pressure prior to administration may not be more than about 20 mmHg. For example, the mean increase in systolic blood pressure during administration compared to systolic blood pressure prior to administration may not be more than about 15 mmHg.

During administration of the compound of formula I or pharmaceutically acceptable derivative thereof the mean increase in diastolic blood pressure during administration compared to diastolic blood pressure prior to administration may not increase by more than about 10 mmHg. For example, the mean increase in diastolic blood pressure during administration compared to diastolic blood pressure prior to administration may not increase by more than about 5 mmHg.

The patient's base line blood pressure in a sedentary state may be taken as the patient's blood pressure prior to administration. Blood pressure readings including base readings may be determined according to standard procedures (see for example Pickering and Stevens, How to measure and record blood pressure, Community Eye Health, 2013, 26(84), 76). In order to determine the mean increases in systolic and diastolic blood pressure, the sample will usually be a random sample of at least 10 patients, preferably at least 100 patients. Preferably the mean increase in blood pressure will be determined during a clinical trial, in particular a phase 3 clinical trial.

The compound of formula I or pharmaceutically acceptable derivative thereof may be administered to the patient such that the blood plasma concentration ($C_{max}$) of the compound of formula I (i.e. the active moiety, e.g. the compound of formula I-A) remains below about 450 ng/ml. The compound of formula I or pharmaceutically acceptable derivative thereof may be administered to the patient such that the blood plasma concentration ($C_{max}$) of the compound of formula I (i.e. the active moiety, e.g. the compound of formula I-A) does not increase above about 300 ng/ml. The compound of formula I or pharmaceutically acceptable derivative thereof may be administered to the patient such that the blood plasma concentration ($C_{max}$) of the compound of formula I (i.e. the active moiety, e.g. the compound of formula I-A) does not increase above about 250 ng/ml.

The compound of formula I or pharmaceutically acceptable derivative thereof may be administered at a dose such that the mean blood plasma concentration ($C_{max}$) of the compound of formula I (i.e. the active moiety, e.g. the compound of formula I-A) remains below about 450 ng/ml. The compound of formula I or pharmaceutically acceptable derivative thereof may be administered at a dose such that the mean blood plasma concentration ($C_{max}$) of the compound of formula I (i.e. the active moiety, e.g. the compound of formula I-A) does not increase above about 300 ng/ml. The compound of formula I or pharmaceutically acceptable derivative thereof may be administered at a dose such that the mean blood plasma concentration ($C_{max}$) of the compound of formula I (i.e. the active moiety, e.g. the compound of formula I-A) does not increase above about 250 ng/ml.

In order to determine the mean increase in blood plasma concentration ($C_{max}$) of the compound of formula I, the sample will usually be a random sample of at least 10 patients, preferably at least 100 patients. Preferably the mean increase in blood plasma concentration ($C_{max}$) will be determined during a clinical trial, in particular a phase 3 clinical trial.

A further aspect of the invention provides a compound of formula I or pharmaceutical derivative thereof, which may be the dihydrochloride salt of the compound of formula I-B, for use in the treatment of a neoplastic disease in a patient, wherein said compound or pharmaceutically acceptable derivative thereof is intravenously administered to said patient, preferably by continuous infusion, over a period of more than 2 hours, and wherein the dose of the compound of formula I or pharmaceutically acceptable derivative thereof is at least the molar equivalent of about 45 mg/m² of the dihydrochloride salt of the compound formula I-B and wherein the patient's blood plasma concentration ($C_{max}$) of the compound of formula I does not increase above about 450 ng/ml. In one embodiment the patient's blood plasma concentration ($C_{max}$) of the compound of formula I does not increase above about 300 ng/ml. In another embodiment the patient's blood plasma concentration ($C_{max}$) of the compound of formula I does not increase above about 250 ng/ml.

A further aspect of the invention provides a pharmaceutical composition for intravenous administration comprising the compound of formula I or pharmaceutically acceptable derivative thereof in an amount that is at least the molar equivalent of 160 mg of the dihydrochloride salt of the compound of formula I-B, in saline solution and/or Ringer lactate solution, preferably Ringer lactate solution. In one embodiment pharmaceutical composition comprises the compound of formula I or pharmaceutically acceptable derivative thereof in an amount that is at least the molar equivalent 230 mg of the dihydrochloride salt of the compound of formula I-B.

In a further aspect the invention provides a method of preparing a pharmaceutical composition for intravenous administration, comprising the step of reconstituting an amount of the compound of formula I or pharmaceutically acceptable derivative thereof that is at least the molar equivalent of 160 mg of the dihydrochloride salt of the compound of formula I-B e.g. in saline solution and/or Ringer lactate solution, preferably Ringer lactate solution. In one embodiment the amount of the compound of formula I or pharmaceutically acceptable derivative thereof is at least the molar equivalent of 230 mg of the dihydrochloride salt of the compound of formula I-B.

In a further aspect the invention provides a method of preparing a pharmaceutical composition for intravenous administration, comprising the step of reconstituting an amount of the compound of formula I or pharmaceutically acceptable derivative thereof that is at least the molar equivalent of 50 mg of the dihydrochloride salt of the compound of formula I-B e.g. in saline solution and/or Ringer lactate solution, preferably Ringer lactate solution and the step of filling a pump for continuous infusion with the reconstituted compound of formula I or pharmaceutically acceptable derivative thereof. In one embodiment the method of preparing a pharmaceutical composition for intravenous administration comprises reconstituting an amount of the compound of formula I or pharmaceutically acceptable derivative thereof that is at least the molar equivalent of 70 mg of the dihydrochloride salt of the compound of formula I-B. In another embodiment the method of preparing a pharmaceutical composition for intravenous administration comprises reconstituting at least an amount of the compound of formula I or pharmaceutically acceptable derivative thereof that is at least the molar equivalent of 110 mg of the dihydrochloride salt of the compound of formula I-B. In another embodiment the method of preparing a pharmaceutical composition for intravenous administration comprises reconstituting an amount of the compound of formula I or pharmaceutically acceptable derivative thereof that is at least the molar equivalent of 160 mg of the dihydrochloride salt of the compound of formula I-B. In another embodiment the method of preparing a pharmaceutical composition for intravenous administration comprises reconstituting an amount of the compound of formula I or pharmaceutically acceptable derivative thereof that is at least the molar equivalent of 230 mg of the dihydrochloride salt of the compound of formula I-B.

In a further aspect the invention provides a continuous infusion pump comprising a pharmaceutical composition, wherein said pharmaceutical composition comprises an amount of the compound of formula I or pharmaceutically acceptable derivative thereof that is at least the molar equivalent of 50 mg of the dihydrochloride salt of the compound of formula I-B, preferably in saline and/or Ringer lactate solution, preferably Ringer lactate solution. In one embodiment the pharmaceutical composition comprises an amount of the compound of formula I or pharmaceutically acceptable derivative thereof that is at least the molar equivalent of 70 mg of the dihydrochloride salt of the compound of formula I-B. In another embodiment the pharmaceutical composition comprises an amount of the compound of formula I or pharmaceutically acceptable derivative thereof that is at least the molar equivalent of 110 mg of the dihydrochloride salt of the compound of formula I-B. In another embodiment the pharmaceutical composition comprises an amount of the compound of formula I or pharmaceutically acceptable derivative thereof that is at least the molar equivalent of 160 mg of the dihydrochloride salt of the compound of formula I-B. In another embodiment the pharmaceutical composition comprises an amount of the compound of formula I or pharmaceutically acceptable derivative thereof that is at least the molar equivalent of 230 mg of the dihydrochloride salt of the compound of formula I-B.

In a further aspect the invention provides a kit for administering to a patient suffering from a neoplastic disease a compound of formula I or a pharmaceutically acceptable derivative thereof, which pharmaceutically acceptable derivative may be the dihydrochloride salt of the compound of formula I-B, comprising a sterile container comprising an amount of the compound of formula I or pharmaceutically acceptable derivative thereof that is at least the molar equivalent of 50 mg of the dihydrochloride salt of the compound of formula I-B, preferably in powder (e.g. lyophilized) form, and a pump for continuous infusion, preferably an elastomeric pump. The kit may also include saline solution and/or Ringer lactate solution, preferably Ringer lactate solution, for reconstituting the compound of formula I or pharmaceutically acceptable derivative thereof. In one embodiment the sterile container comprises an amount of the compound of formula I or pharmaceutically derivative thereof that is at least the molar equivalent of 70 mg of the dihydrochloride salt of the compound of formula I-B. In another embodiment the sterile container comprises an amount of the compound of formula I or pharmaceutically derivative thereof that is at least the molar equivalent of 110 mg of the dihydrochloride salt of the compound of formula I-B. In another embodiment the sterile container comprises an amount of the compound of formula I or pharmaceutically derivative thereof that is at least the molar equivalent of 160 mg of the dihydrochloride salt of the compound of formula I-B. In another embodiment the sterile container comprises an amount of the compound of formula I or pharmaceutically derivative thereof that is at least the molar equivalent of 230 mg of the dihydrochloride salt of the compound of formula I-B. The kit may include a cannula and/or administration tube or other conuit for delivering the compound of formula I or pharmaceutically acceptable derivative thereof into the patient's body. The kit may also include instructions for reconstituting the compound of formula I or pharmaceutically acceptable derivative thereof to provide a dose corresponding to at least the required molar equivalent of the dihydrochloride salt of the compound of formula I-B and optionally for filling the pump with the reconstituted compound of formula I or pharmaceutically acceptable derivative thereof.

The term "treatment" as used herein in the context of treating a neoplastic disease in a patient pertains generally to treatment and therapy in which some desired therapeutic effect is achieved, for example, the inhibition of the progress of the neoplastic disease, and includes a reduction in the rate of progress, a halt in the rate of progress, alleviation of symptoms of the neoplastic disease, amelioration of neoplastic disease, and cure of the neoplastic disease. The patient as referred to herein is a human patient, preferably a human cancer patient.

In particular, compounds of the invention may be used to prevent or inhibit the progression of a cancer at various stages (e.g. tumor stage I, tumor stage II, tumor stage III, tumor stage IV) or treatment settings (e.g. preventative, adjuvant, neoadjuvant, therapeutic including palliative treatment). A compound of the invention may be for use in slowing, delaying or stopping cancer progression or cancer growth or increasing the overall survival time or the cancer-progression-free survival time or the time to progression of a cancer or improving or maintaining the patient's quality of life or functional status.

The compounds according to formula I and pharmaceutically acceptable derivatives thereof may be used for the therapeutic treatment of neoplastic diseases. Examples of neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

In an especially preferred embodiment the neoplastic disease is cancer. Examples of cancers in terms of the organs and parts of the body affected include, but are not limited to, the brain, breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis.

Preferably the cancer is selected from the group consisting of brain cancer (e.g. glioblastoma), breast cancer (including triple negative breast cancer), prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

In one embodiment the cancer to be treated is a tumor, preferably a solid tumor.

In a further embodiment the neoplastic disease is a brain neoplasm, e.g. a brain tumor, which include but are not limited to glial- and non-glial-tumors, astrocytomas (incl. glioblastoma multiforme and unspecified gliomas), oligodendrogliomas, ependydomas, menigiomas, haemangioblastomas, acoustic neuromas, craniopharyngiomas, primary central nervous system lymphoma, germ cell tumors, pituitary tumors, pineal region tumors, primitive neuroectodermal tumors (PNET's), medullablastomas, haemangiopericytomas, spinal cord tumors including meningiomas, chordomas and genetically-driven brain neoplasms including neurofibromatosis, peripheral nerve sheath tumors and tuberous sclerosis. Preferably, brain neoplasm refers to glioblastomas (also referred to as glioblastoma multiforme).

A compound of formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents.

A compound of formula I or a pharmaceutically acceptable derivative thereof can, besides or in addition, be administered especially for tumor therapy in combination with chemotherapy (cytotoxic therapy), targeted therapy, endocrine therapy, biologics, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In all aspects and embodiments of the invention the compound referred to is preferably the compound of formula I-B and pharmaceutically acceptable salts thereof, and in particular dihydrochloride salt of the compound of formula I-B.

The term "about" means a variation of no more than 10% of the relevant figure, preferably no more than 5%.

All aspects and embodiments of the invention described herein may be combined in any combination. All references are hereby incorporated by reference.

The following non-limiting examples illustrate the invention.

EXAMPLES

Clinical Trial Methodology

In one clinical trial BAL101553 (dihydrochloride salt) was given as a 2-hour infusion on days 1, 8, and 15 of each 28-day cycle (comparative Example).

In another clinical trial BAL101553 (dihydrochloride salt) was given as a 48-hour infusion on days 1, 8 and 15 of each 28 day cycle.

In another clinical trial BAL101553 (dihydrochloride salt) was given as a daily oral administration in treatment cycles consisting of 28 days of continuous, daily administration to patients in a fasted state (comparative Example).

BAL101553 (dihydrochloride salt) for intravenous administration is prepared by reconstitution of lyophilized BAL101553 (dihydrochloride salt) with saline solution or Ringer lactate solution, prior to further dilution with Ringer lactate for intravenous infusion to the patient. The 48-hour infusion is administered via an elastomeric pump (Baxter) using an infusion volume of 120 ml or 240 ml.

BAL101553 (dihydrochloride salt) for oral administration is prepared as a HPMC capsules containing 1 mg active ingredient, 98 mg of mannitol and 1 mg magnesium stearate, or 5 mg active ingredient, 94 mg mannitol and 1 mg magnesium stearate.

The maximum tolerated dose (MTD) of the 48-hour infusion administration clinical trial described above was declared as 70 mg/m².

The maximum tolerated dose (MTD) of the daily oral administration clinical trial described above was declared as 16 mg/day.

Evaluation of Plasma Drug Concentrations in Patients Treated with BAL101553

2-hour intravenous infusion study: on day 1 of cycle 1 blood samples were collected at pre-dose and where clinically feasible 0.5, 1, 2, 3, 4, 6, 8 and 24 hours after dosing.

48-hour intravenous infusion study: on day 1 of cycle 1 blood samples were collected at pre-dose and where clinically feasible 0.5, 1, 2, 4, 8, 24, 30, 48, 52, 54, 72, and 168 hours after dosing.

Daily oral administration study: on day 1 of cycle 1 blood samples were collected at pre-dose and where clinically feasible 0.5, 1, 2, 3, 4, 6, 8 and 24 hours after intake of study medication.

Venous blood samples were collected into chilled 2 ml plastic tubes containing K2-EDTA as an anticoagulant mixed with 20 µl 2M citric acid and kept on ice for 15 minutes. Approximately 1.0 ml plasma was prepared by centrifugation at 1'500×g for 10-15 minutes at 4° C., transferred into new vials and stored at −80° C. until analysis. Plasma concentrations of BAL27862 were determined with a fully validated LC-MS/MS method:

50 µl of acetonitrile was added to 25 µl plasma containing stable labelled internal standards (IS). After vortexing, the samples were centrifuged for 10 minutes at 50'000×g at 8° C. and 50 µl of the supernatant was transferred to an empty auto-sampler vial. The extract was separated by liquid chromatography, performed using water (0.1% formic acid) as mobile phase A and acetonitrile (0.1% formic acid) as mobile phase B. The column used was a YMC Hydrosphere C18, 2.1×33 mm, 3 µm (YMC Co, Kyoto, Japan). The injection volume was set to 2 µL (full loop).

Detection was carried out using a triple-stage quadrupole MS/MS (TSQ Vantage, Thermo Fisher Scientific, San Jose, Calif., USA) in the selected reaction monitoring mode.

The following calibration range was applied:

1 to 1000 ng/ml for BAL27862 in human plasma (K3-EDTA, citric acid)

Calculation of Pharmacokinetic Parameters (exposure [Area Under the Curve—AUC] and peak [$C_{max}$] drug levels) for Human Samples:

AUC and $C_{max}$ of BAL27862 were calculated by non-compartmental analysis (NCA) using Phoenix WinNonLin 7.0 software from Certara.

Figure 2:
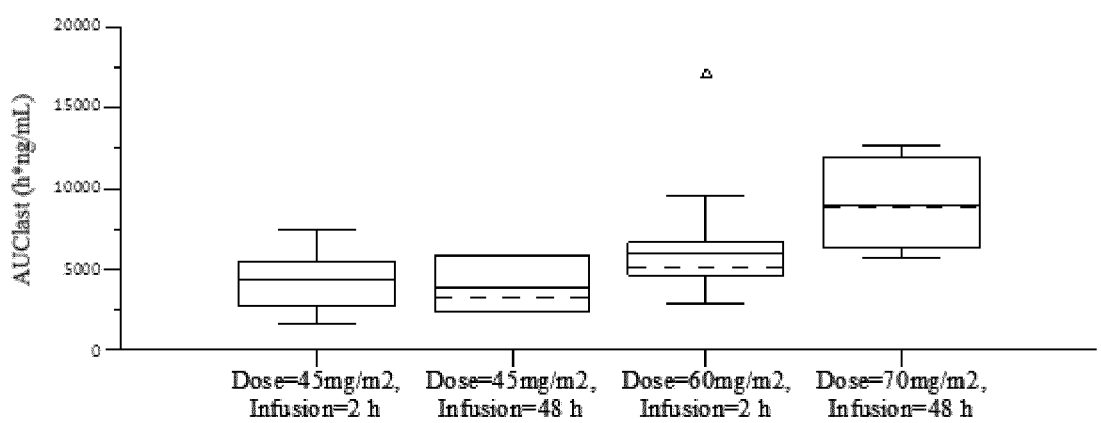
FIG. 2 shows the Area Under the Curve (AUC) results of BAL27862 from patients administered with the dihydrochloride salt of BAL101553 as a 2-hour intravenous infusion and patients administered with the dihydrochloride salt of BAL101553 as a 48-hour intravenous infusion. In the box and whiskers plots the box represents 25th and 75th percentiles (interquartile range, IQR), inside the box the solid line is the arithmetic mean and the dashed line is the median; the whiskers represent 1.5×IQR or min/max range; individual data points outside the IQR whiskers are shown as individual dot outliers.

Results are shown in Table 1 below and the data is depicted in FIGS. 1 and 2.

TABLE 1

| | | Infusion | | | |
| --- | --- | --- | --- | --- | --- |
| | | 2 hours | | 48 hours | |
| Dose | Subject | Cmax (ng/m) | AUClast (h*ng/m) | Cmax (ng/m) | AUClast (h*ng/m) |
| 45 mg/m² | N | 8 | 8 | 3 | 3 |
| | Mean | 356 | 4340 | 77.7 | 3830 |
| 60 mg/m² | N | 21 | 21 | | |
| | Mean | 498 | 6040 | nt | nt |
| 70 mg/m² | N | | | 4 | 4 |
| | Mean | nt | nt | 152 | 9030 |
| 90 mg/m² | N | | | 4 | 4 |
| | Mean | nt | nt | 238 | 12000 | nt = not tested

Comparison of BAL101553 Administration by 48 Hour Continuous Infusion Versus Daily Oral Administration Table 2 shows a comparison of the PK results and serious Grade 4 adverse drug reactions for BAL101553 administration by 48 hour continuous infusion versus daily oral administration. This data illustrate the safety and efficacy benefit of continuous infusion over daily oral administration of BAL101553 at comparable weekly pharmacokinetic exposure levels of BAL27862.

From a safety perspective, the advantage of the 48-hour infusion regime is evident through the avoidance of serious Grade 4* drug-related adverse reactions (i.e. Grade 4 hyponatremia*) at doses above the MTD. At a daily oral dose of 20 mg/day (supra-MTD), serious Grade 4 hyponatremia has been observed in 2 patients and this was the most serious and relevant toxicity observed with BAL101553 and was only observed with the daily oral administration. The selection of the MTD for the daily oral regimen (i.e. MTD of 16 mg/day) was based on the observation of the above-mentioned serious Grade 4 hyponatremia cases. At a dose of 90 mg/m² (supra-MTD) with a 48-hour infusion regimen, which provides similar or higher weekly exposure compared to 20 mg/day oral administration, there was no observation of Grade 4 hyponatremia. The selection of the MTD for the 48-hour infusion regimen (i.e. MTD of 70 mg/m²) was based on the observation of less severe side effects.

The advantage of the 48-hour infusion regimen over the daily oral regimen is further supported by observation of a partial tumour response in a patient at the MTD dose (70 mg/m²), while no objective responses were observed with the daily oral dose regimen at any dose.

The 48-hour dose regimen was furthermore associated with a lower variability of pharmacokinetic exposure (AUC).

TABLE 2

|  | Daily oral, 16 mg N = 7 | Daily oral, 20 mg N = 7 | 48-hour infusion, 70 mg/m² N = 9 | 48-hour infusion, 90 mg/m² N = 4 |
|---|---|---|---|---|
| Cmax (mean, ng/ml) | 131 | 134 | 148 | 238 |
| AUC (mean, h*ng/ml) | 8400 | 12180 | 8580 | 13500 |
| Serious Grade 4 adverse drug reactions | None | 2 patients with serious Grade 4 hyponatremia | None | None |

*According to CTCAE Grade 4 adverse events are generally defined as "Life-threatening consequences; OR urgent intervention indicated". For the event "hyponatremia" Grade 4 events are defined as hyponatremia that is life-threatening or characterized by sodium blood levels <120 mmol/L.
Source: Common Terminology Criteria for Adverse Events (CTCAE) Version 4.0, Published: May 28, 2009 (v 4.03 June 2014, 2010).

Blood Pressure Measurements in Patients Treated with BAL101553

On day 1 of cycle 1 of the 2-hour and 48-hour intravenous infusion studies systolic and diastolic blood pressures were measured using a calibrated, automated blood pressure device at various time points, i.e. prior to the first administration of study drug and then at least hourly for the first 4 hours after start of dosing.

Figure 3:
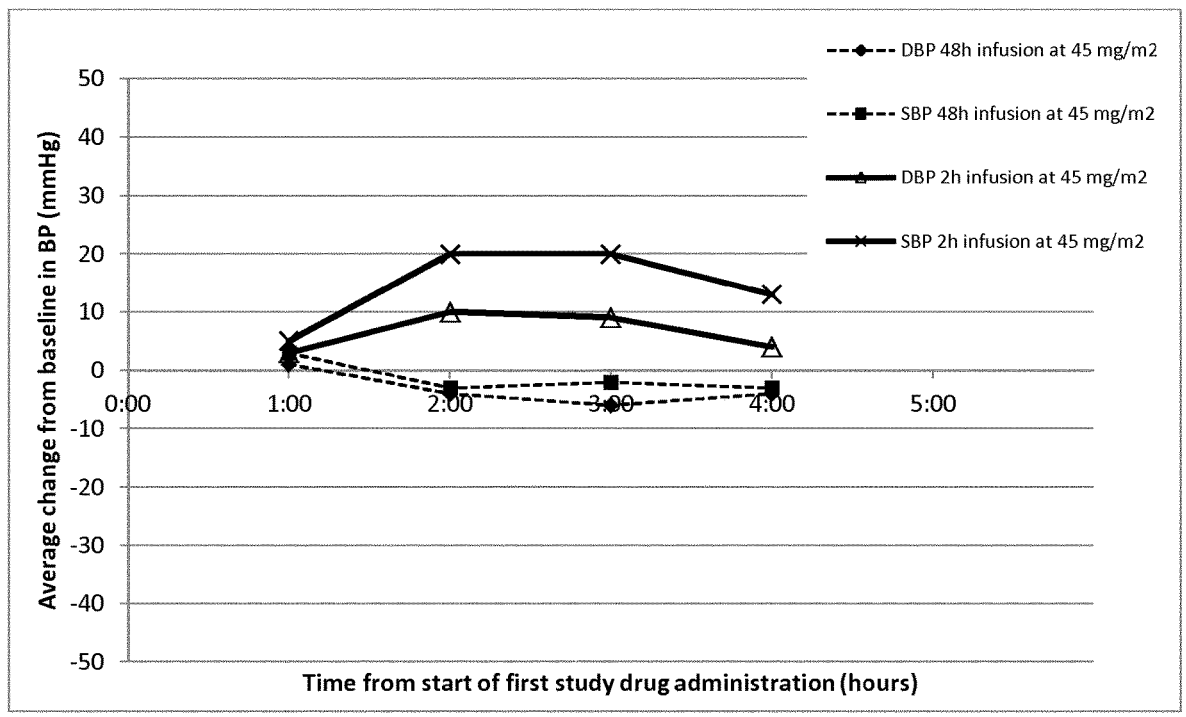
FIG. 3 shows a comparison of the average change from baseline (pre-dose) in systolic blood pressure (SBP) and diastolic blood pressure (DBP) in patients treated at a dose level of 45 mg/m² using a 2-hour intravenous infusion (solid lines, N=8) or a 48-hour infusion (dotted line, N=3) of BAL101553.
Figure 4:
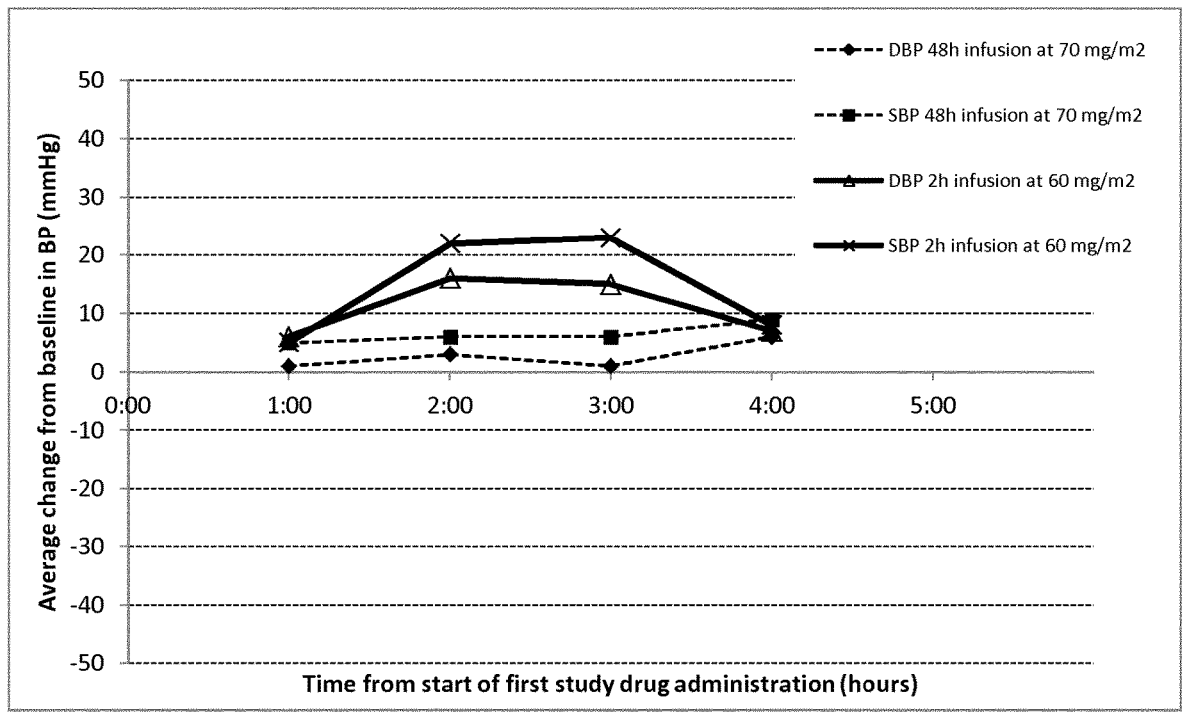
FIG. 4 shows a comparison of the average change from baseline (pre-dose) in systolic blood pressure (SBP) and diastolic blood pressure (DBP) in patients treated at a dose level of 60 mg/m² using a 2-hour intravenous infusion (solid lines, N=21) or of 70 mg/m² using a 48-hour infusion (dotted line, N=3) of BAL101553.
Figure 5:
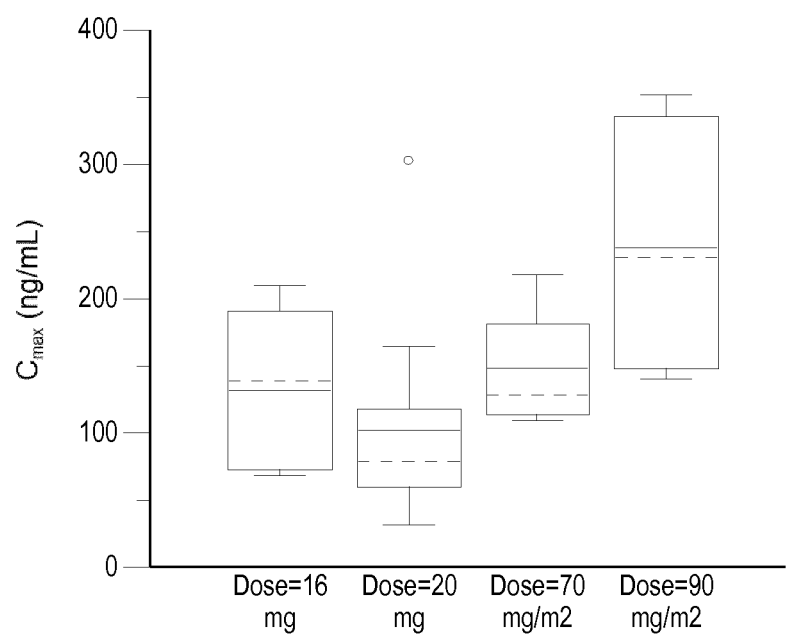
FIG. 5 shows a comparison of the $C_{max}$ results of BAL27862 from patients administered with the dihydrochloride salt of BAL101553 as a 16 mg and 20 mg daily oral administration and patients administered with the dihydrochloride salt of BAL101553 as a 70 mg/m² and 90 mg/m² 48-hour intravenous infusion. In the box and whiskers plots the box represents $25^{th}$ and $75^{th}$ percentiles (interquartile range, IQR), inside the box the solid line is the arithmetic mean and the dashed line is the median; the whiskers represent 1.5×IQR or min/max range; individual data points outside the IQR whiskers are shown as individual dot outliers.
Figure 6:
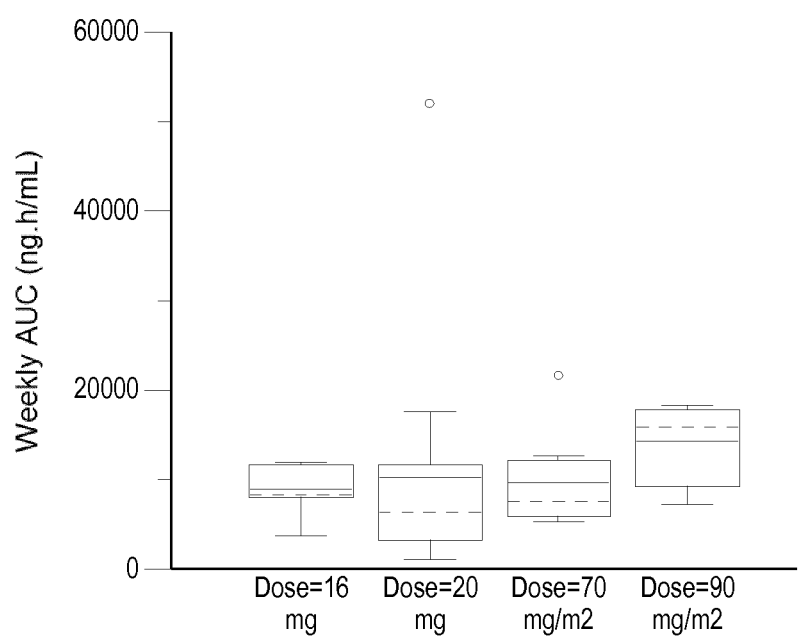
FIG. 6 shows a comparison of the Area Under the Curve (AUC) results of BAL27862 from patients administered with the dihydrochloride salt of BAL101553 as a 16 mg and 20 mg daily oral administration and patients administered with the dihydrochloride salt of BAL101553 as a 70 mg/m² and 90 mg/m² 48-hour intravenous infusion. In the box and whiskers plots the box represents $25^{th}$ and $75^{th}$ percentiles (interquartile range, IQR), inside the box the solid line is the arithmetic mean and the dashed line is the median; the whiskers represent 1.5×IQR or min/max range; individual data points outside the IQR whiskers are shown as individual dot outliers.

The data is shown in FIGS. 3 and 4. It can be seen that the duration of BAL101553 infusion at a given dose level provides different effects on blood pressure as an expression of vascular effects. A neutral blood pressure profile or a minor average change from baseline is noted when BAL101553 is infused over 48 hours. In contrast a short infusion duration of 2 hours results in distinct changes from baseline in both systolic and diastolic blood pressure. The differences in effects on blood pressure are evident for a dose level of 45 mg/m² (2-hour infusion and 48-hour infusion) (see FIG. 3) and for 60 mg/m² (2-hour infusion) or 70 mg/m² (48-hour infusion) (see FIG. 4). This different behavior may be explained through a pharmacokinetic-toxicity relationship, in the sense that vascular effect are driven by the maximum plasma concentration which is higher with the 2-hour infusion versus the 48-hour infusion.

Three patients treated at 45 mg/m² or 60 mg/m² using a 2-hour infusion were found to have a troponin elevation indicative of myocardial damage, while such toxicity was not observed at 45 mg/m² or 70 mg/m² when using a 48-hour infusion. This may be due to a vascular toxic effect on the heart, which varies at a given dose-level depending on the duration of study drug infusion. This would be consistent with the blood pressure observations.

The invention claimed is:

1. A method of treating a neoplastic disease, comprising the step of administering a compound of formula I:

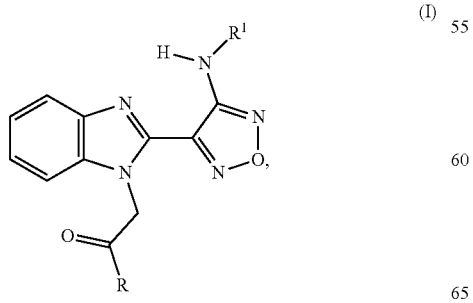

(I)

wherein:
R represents phenyl or pyridinyl;
wherein phenyl is optionally substituted by one or two substituents independently selected from lower alkyl, lower alkoxy, hydroxyl, amino, lower alkylamino, lower dialkylamino, acetylamino, halogen and nitro;
and wherein pyridinyl is optionally substituted by amino or halogen;
$R^1$ represents hydrogen or cyano-lower alkyl;
and wherein the prefix lower denotes a radical having up to and including a maximum of 4 carbon atoms;
or a pharmaceutically acceptable derivative thereof;
to a patient in need thereof, which pharmaceutically acceptable derivative is a pharmaceutically acceptable salt, pro-drug or pharmaceutically acceptable salt of a pro-drug thereof, wherein the pro-drug is an amide formed from an amino group present within the R group of the compound of formula I and the carboxy group of glycine, alanine or lysine,
wherein said compound of formula I or pharmaceutically acceptable derivative thereof is intravenously administered to said patient over a period of at least about 8 hours, wherein the dose of the compound of formula I or a pharmaceutically acceptable derivative thereof is at least the molar equivalent of about 45 mg/m² of the dihydrochloride salt of the compound of formula I-B

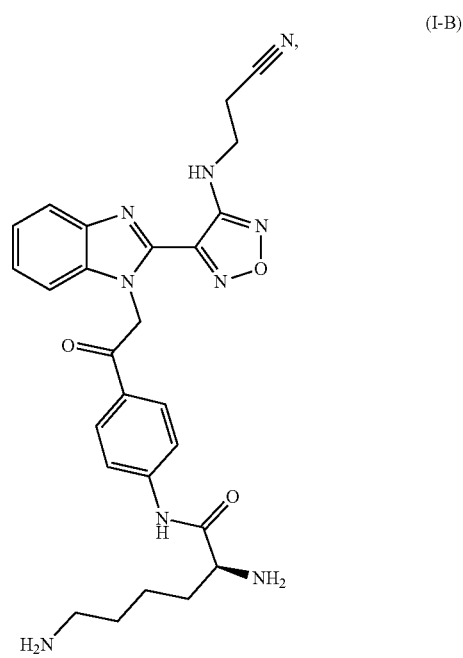 [SMILES: N#CCCNc1nonc1-c1nc2ccccc2n1CC(=O)c1ccc(NC(=O)[C@@H](N)CCCCN)cc1]

(I-B)

wherein the neoplastic disease is selected from epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

2. The method of claim 1, wherein the compound of formula I or pharmaceutically acceptable derivative thereof is intravenously administered to the patient by continuous infusion over a period of at least about 24 hours.

3. The method of claim 1, wherein the compound of formula I or pharmaceutically acceptable derivative thereof is intravenously administered to the patient by continuous infusion over a period of at least about 48 hours.

4. The method of claim 1, wherein the dose of the compound of formula I or pharmaceutically acceptable derivative thereof is at least the molar equivalent of about 60 mg/m$^2$ of the dihydrochloride salt of the compound of formula I-B.

5. The method of claim 1, wherein the dose of the compound of formula I or pharmaceutically acceptable derivative thereof is at least the molar equivalent of about 70 mg/m$^2$ of the dihydrochloride salt of the compound of formula I-B.

6. The method of claim 1, wherein the dosage volume is at least about 100 ml.

7. The method of claim 1, wherein the dosage volume is at least about 200 ml.

8. The method of claim 1, wherein the compound of formula I or pharmaceutically acceptable derivative thereof is administered according to a 28 day treatment cycle and administration commences on days 1, 8 and 15.

9. The method of claim 1, wherein the blood plasma concentration (C max) of the compound of formula I in the patient remains below about 450 ng/ml.

10. The method of claim 1, wherein the blood plasma concentration (C max) of the compound of formula I in the patient does not increase above about 300 ng/ml.

11. The method of claim 1, wherein the blood plasma concentration (C max) of the compound of formula I in the patient does not increase above about 250 ng/ml.

12. The method of claim 1, wherein the compound of formula I is the compound of formula I-A:

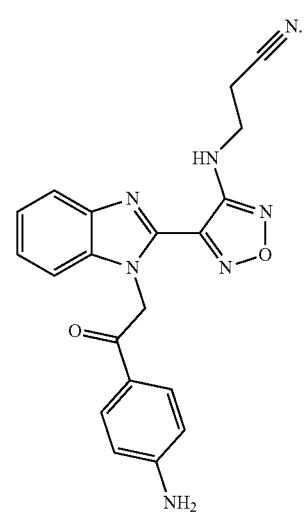

(I-A)

or a pharmaceutically acceptable derivative thereof.

13. The method of claim 1, wherein the compound of formula I or pharmaceutically acceptable derivative thereof is the compound of formula I-B or a pharmaceutically acceptable salt thereof.

14. The method of claim 13, wherein the compound of formula I-B or pharmaceutically acceptable salt thereof is administered to the patient by continuous infusion over a period of about 48 hours and wherein the dose of the compound of formula I-B or pharmaceutically acceptable salt thereof is at least the molar equivalent of about 70 mg/m$^2$ of the dihydrochloride salt of the compound formula I-B.

15. The method of claim 14, wherein the compound of formula I-B or pharmaceutically acceptable salt thereof is administered according to a 28 day treatment cycle and administration commences on days 1, 8 and 15.

16. The method of claim 15, wherein the blood plasma concentration (C max) of the compound of formula I-A

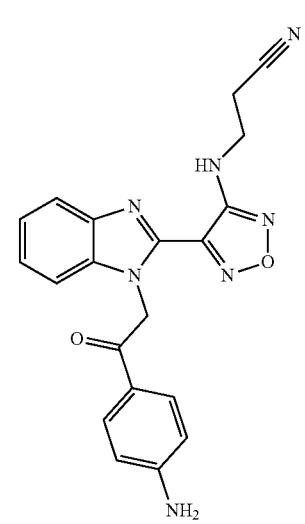

(I-A)

in the patient remains below about 450 ng/ml.

17. The method of claim 15, wherein the blood plasma concentration (C max) of the compound of formula I-A

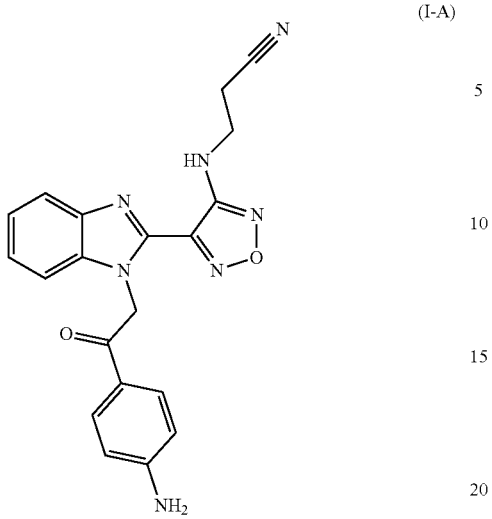
(I-A)

in the patient does not increase above about 300 ng/ml.

18. The method of claim 15, wherein the blood plasma concentration (C max) of the compound of formula I-A in the patient does not increase above about 250 ng/ml,

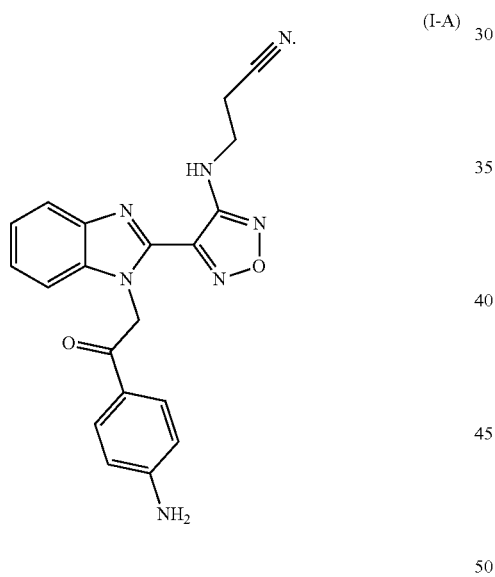
(I-A)

19. The method of claim 1, wherein the compound of formula I or pharmaceutically acceptable derivative thereof is the dihydrochloride salt of the compound of formula I-B.

20. The method of claim 19, wherein the dihydrochloride salt of the compound of formula I-B is administered to the patient by continuous infusion over a period of about 48 hours and wherein the dose of the compound of formula I-B or pharmaceutically acceptable salt thereof is about 70 mg/m².

21. The method of claim 20, wherein the dihydrochloride salt of the compound of formula I-B is administered according to a 28 day treatment cycle and administration commences on days 1, 8 and 15.

22. The method of claim 21, wherein the blood plasma concentration (C max) of the compound of formula I-A

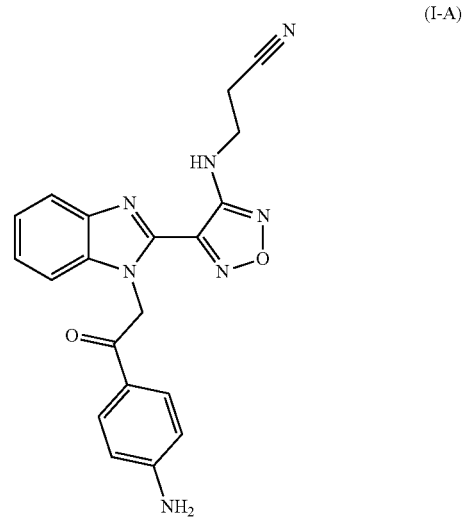 [SMILES: N#CCCNc1nonc1-c1nc2ccccc2n1CC(=O)c1ccc(N)cc1]
(I-A)

in the patient remains below about 450 ng/ml.

23. The method of claim 21, wherein the blood plasma concentration (C max) of the compound of formula I-A

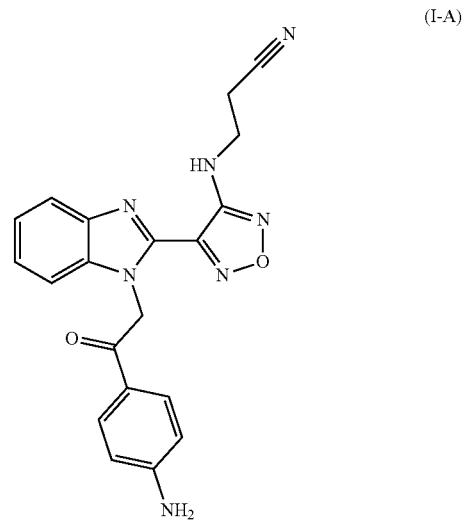 [SMILES: N#CCCNc1nonc1-c1nc2ccccc2n1CC(=O)c1ccc(N)cc1]
(I-A)

in the patient does not increase above about 300 ng/ml.

24. The method of claim 21, wherein the blood plasma concentration (C max) of the compound of formula I-A:

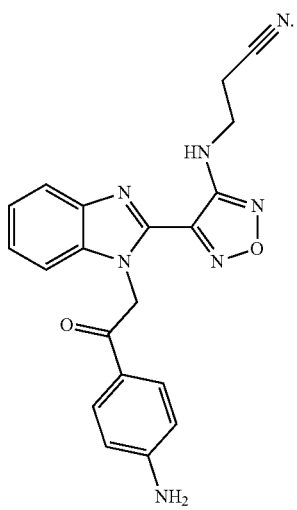

(I-A)

in the patient does not increase above about 250 ng/ml.

25. The method of claim 1, wherein the neoplastic disease is cancer and the cancer in terms of the organs and parts of the body affected is selected from the brain, breast, cervix, ovaries, colon, rectum, lung, endocrine system, bone, adrenal gland, thymus, liver, stomach, intestine, pancreas, bone marrow, hematological malignancies, bladder, urinary tract, kidneys, skin, thyroid, brain, head, neck, prostate and testis.

26. The method of claim 1, wherein the neoplastic disease is cancer and the cancer is selected from the group consisting of brain cancer, breast cancer, prostate cancer, cervical cancer, ovarian cancer, gastric cancer, colorectal cancer, pancreatic cancer, liver cancer, neuroendocrine cancer, lung cancer, kidney cancer, hematological malignancies, melanoma and sarcomas.

27. A method of treating a neoplastic disease, comprising the step of administering a compound of formula I:

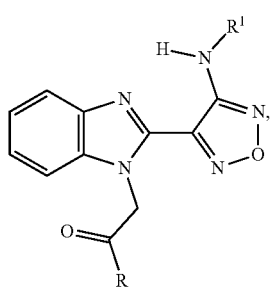

(I)

wherein: R represents phenyl or pyridinyl; wherein phenyl is optionally substituted by one or two substituents independently selected from lower alkyl, lower alkoxy, hydroxyl, amino, lower alkylamino, lower dialkylamino, acetylamino, halogen and nitro; and wherein pyridinyl is optionally substituted by amino or halogen; R' represents hydrogen or cyano-lower alkyl; and wherein the prefix lower denotes a radical having up to and including a maximum of 4 carbon atoms: or a pharmaceutically acceptable derivative thereof; to a patient in need thereof, which pharmaceutically acceptable derivative is a pharmaceutically acceptable salt, pro-drug or pharmaceutically acceptable salt of a pro-drug thereof, wherein the pro-drug is an amide formed from an amino group present within the R group of the compound of formula I and the carboxy group of glycine, alanine or lysine, wherein said compound of formula I or pharmaceutically acceptable derivative thereof is intravenously administered to said patient over a period of at least about 8 hours, wherein the dose of the compound of formula I or a pharmaceutically acceptable derivative thereof is at least the molar equivalent of about 45 mg/m$^2$ of the dihydrochloride salt of the compound of formula I-B

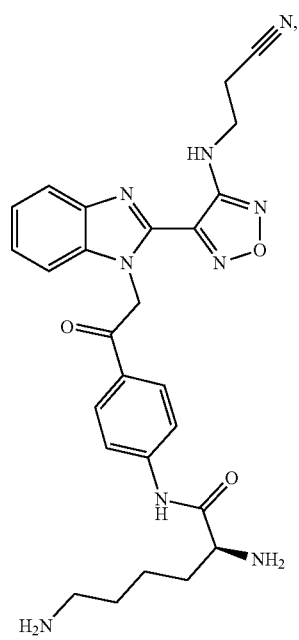

(I-B)

wherein the neoplastic disease is solid tumor.

28. The method of claim 1, wherein the neoplastic disease is a brain neoplasm selected from brain tumor, astrocytomas, oligodendrogliomas, ependydomas, menigiomas, haemangioblastomas, acoustic neuromas, craniopharyngiomas, primary central nervous system lymphoma, germ cell tumors, pituitary tumors, pineal region tumors, primitive neuroectodermal tumors (PNETs), medullablastomas, haemangiopericytomas, spinal cord tumors including meningiomas, chordomas and genetically-driven brain neoplasms including neurofibromatosis, peripheral nerve sheath tumors and tuberous sclerosis.

29. The method of claim 28, wherein the brain neoplasm is glioblastoma.

30. The method of claim 16, wherein the neoplastic disease is cancer and the cancer in terms of the organs and parts of the body affected is selected from the brain, breast, cervix, ovaries, colon, rectum, lung, endocrine system, bone, adrenal gland, thymus, liver, stomach, intestine, pancreas, bone marrow, hematological malignancies, bladder, urinary tract, kidneys, skin, thyroid, brain, head, neck, prostate and testis.

31. The method of claim 16, wherein the neoplastic disease is cancer and the cancer is selected from the group consisting of brain cancer, breast cancer, prostate cancer, cervical cancer, ovarian cancer, gastric cancer, colorectal cancer, pancreatic cancer, liver cancer, neuroendocrine cancer, lung cancer, kidney cancer, hematological malignancies, melanoma and sarcomas.

32. The method of claim 30, wherein the cancer to be treated is a solid tumor.

33. The method of claim 16, wherein the neoplastic disease is a brain neoplasm selected from brain tumor, astrocytomas, oligodendrogliomas, ependydomas, menigiomas, haemangioblastomas, acoustic neuromas, craniopharyngiomas, primary central nervous system lymphoma, germ cell tumors, pituitary tumors, pineal region tumors, primitive neuroectodermal tumors (PNETs), medullablastomas, haemangiopericytomas, spinal cord tumors including meningiomas, chordomas and genetically-driven brain neoplasms including neurofibromatosis, peripheral nerve sheath tumors and tuberous sclerosis.

34. The method of claim 33, wherein the brain neoplasm is glioblastoma.

35. The method of claim 1, wherein the compound of formula I is the compound of formula I-A or a pharmaceutically acceptable salt thereof.

36. The method of claim 35, wherein the compound of formula I-A or pharmaceutically acceptable salt thereof is administered to the patient by continuous infusion over a period of about 48 hours and wherein the dose of the compound of formula I-A or pharmaceutically acceptable salt thereof is at least the molar equivalent of about 70 mg/m$^2$ of the dihydrochloride salt of the compound formula I-B.

37. The method of claim 36, wherein the compound of formula I-A or pharmaceutically acceptable derivative thereof is administered according to a 28 day treatment cycle and administration commences on days 1, 8 and 15.

38. The method of claim 37, wherein the blood plasma concentration (C max) of the compound of formula I-A

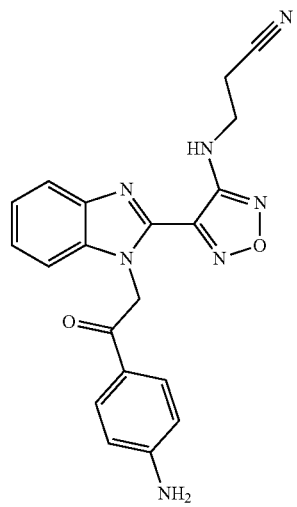

(I-A)

in the patient remains below about 450 ng/ml.

39. The method of claim 37, wherein the blood plasma concentration (C max) of the compound of formula I-A (I-A)

in the patient does not increase above about 300 ng/ml.

40. The method of claim 37, wherein the blood plasma concentration (C max) of the compound of formula I-A (I-A)

in the patient does not increase above about 250 ng/ml.

41. The method of claim 14, wherein the neoplastic disease is a glial tumor.

42. The method of claim 41, wherein the glial tumor is selected from the group consisting of astrocytomas, oligodendrogliomas, ependydomas, and primitive neuroectodermal tumors (PNETs).

43. The method of claim 41, wherein the glial tumor is glioblastoma multiforme.

44. The method of claim 14, wherein the neoplastic disease is medullablastoma.

45. The method of claim 20, wherein the neoplastic disease is a glial tumor.

46. The method of claim 45, wherein the glial tumor is selected from the group consisting of astrocytomas, oligodendrogliomas, ependydomas, and primitive neuroectodermal tumors (PNETs).

47. The method of claim 45, wherein the glial tumor is glioblastoma multiforme.

48. The method of claim 20, wherein the wherein the neoplastic disease is medullablastoma.

49. The method of claim 36, wherein the neoplastic disease is a glial tumor.

50. The method of claim 49, wherein the glial tumor is selected from the group consisting of astrocytoma, oligodendrogliomas, ependydomas, and primitive neuroectodermal tumors (PNETs).

51. The method of claim 49, wherein the glial tumor is glioblastoma multiforme.

52. The method of claim 36, wherein the neoplastic disease is medullablastoma.

* * * * *